United States Patent
Luesch et al.

(10) Patent No.: US 9,492,434 B2
(45) Date of Patent: Nov. 15, 2016

(54) COMBINATION COMPOSITIONS AND METHODS OF TREATMENT

(71) Applicant: University of Florida Research Foundation, Inc., Gainesville, FL (US)

(72) Inventors: Hendrik Luesch, Gainesville, FL (US); Brian Keith Law, Gainesville, FL (US)

(73) Assignee: University of Florida Research Foundation, Inc., Gainesville, FL (US)

(*) Notice: Subject to any disclaimer, the term of this patent is extended or adjusted under 35 U.S.C. 154(b) by 0 days.

(21) Appl. No.: 14/363,730

(22) PCT Filed: Dec. 7, 2012

(86) PCT No.: PCT/US2012/068479
§ 371 (c)(1),
(2) Date: Jun. 6, 2014

(87) PCT Pub. No.: WO2013/086344
PCT Pub. Date: Jun. 13, 2013

(65) Prior Publication Data
US 2014/0323450 A1    Oct. 30, 2014

Related U.S. Application Data

(60) Provisional application No. 61/569,057, filed on Dec. 9, 2011.

(51) Int. Cl.
*A61K 31/426* (2006.01)
*A61K 31/573* (2006.01)
*A61K 31/429* (2006.01)
*A61K 45/06* (2006.01)
*C07D 513/16* (2006.01)

(52) U.S. Cl.
CPC .......... *A61K 31/429* (2013.01); *A61K 31/426* (2013.01); *A61K 31/573* (2013.01); *A61K 45/06* (2013.01); *C07D 513/16* (2013.01)

(58) Field of Classification Search
CPC ................. A61K 31/426; A61K 31/573
See application file for complete search history.

(56) References Cited

U.S. PATENT DOCUMENTS

| | | |
|---|---|---|
| 2010/0029731 A1 | 2/2010 | Williams et al. |
| 2010/0098702 A1 | 4/2010 | Wang et al. |
| 2011/0086869 A1 | 4/2011 | Perrine et al. |
| 2011/0092697 A1 | 4/2011 | Luesch et al. |
| 2011/0118323 A1 | 5/2011 | Luesch et al. |

FOREIGN PATENT DOCUMENTS

WO   WO 2009/032352   *   3/2009

OTHER PUBLICATIONS

Webpage http://www.cancerresearchuk.org/about-cancer/cancers-in-general/treatment/cancer-drugs/steroids Mar. 14, 2016.*
Liu, Y., et al.; "Anticolon Cancer Activity of Largazole, a Marine-Derived Tunable Histone Deacetylase Inhibitor", JPET, Aug. 25, 2010, vol. 335, No. 2, pp. 351-361.
Taori, K., et al; "Structure and Activity of Largazole, a Potent Antiproliferative Agent From the Floridian Marine *Cyanobacterium symploca* sp." JACS, Jan. 19, 2008, vol. 130, No. 6, pp. 1806-1807.
Lee, S.U. et al; "In Vitro and In Vivo Osteogenic Activity of Largazole"; ACS Medical Chemistry Letters, Jan. 4, 2011, vol. 2, No. 3, pp. 248-251.
International Search Report of PCT/US2012/068479 dated Mar. 28, 2013.

* cited by examiner

*Primary Examiner* — Bruck Kifle
(74) *Attorney, Agent, or Firm* — Wolf, Greenfield & Sacks, P.C.

(57) ABSTRACT

The instant invention describes macrocyclic compounds having therapeutic activity, and methods of treating disorders such as methods of modulating cellular proliferation processes, and methods of treating disease, disorders, and symptoms thereof.

15 Claims, 10 Drawing Sheets

Fig. 4 B

IPI00290039 (200%), 92,932.9 Da
isoform 1 of CUB domain containing protein 1
10 unique peptides, 11 unique spectra, 13 total spectra, 100/836 amino acids (12% coverage)

```
MAGLNCGVSI ALLCVLLLGA ARLPRGAEAF EIALPRESNI TYLIKLGTPT LLAKPCYIVI SKRHITMLSI
KSGIRIVFTF SCQSPINMFV ICIQNNIDCM SCPCPFCIVQ LQPSTSLLPT LNRTFIWDVK AMKSIGLCLQ
FSIPRLRQIG PGESCPIDLV HSISGRIDAT VVRIGTFCSN GTVSRIKMQE GVKMAIHLPW FHPRNVSGPS
IANRSSTKRL CTIESVPAE PEGFPEDEIM TWQFYVPAHL RASVSFLNFN LSNCERKEER
VIYTPGSTT NPCVFCLQR GSATLMSANY QSPGIIRLQF QVLVQNPQNL SNKIYVVDLS
NERAMSLTIE PRPVKOSRKF VPGFVVLES RTCSSNLTLT SGSKHSISFL NDDLTRLMN VEKTISWTDH
RYCQRKSYSL QVPSDILHIP VELADESWKL LVPKDRLSLV LVPAQKIQQH TEKPCNISF SYLVASATFS
QDLYFGSFCP CCSIKQIQYK QNISVTLRTI APSFQQIASR QGLMVSFIPY EKCCGVFTVT PDTKSKVYLR
TPNWDRGLPS LTSVSWNISV PRDQYALTF FRIVDLIVIL QRTRAEFIES LSAIGLTICC LDEDVLPKPS
FHHSFWVNI SNCSFTSGKO LDLLESVLTI FRTVDLTVIL SNVYAVICDT MYYGHLLODS SGSFLQPCVD VKKKKKTNK
GPAVGIYNDN INTCMPRQPK KFQKGRKDND SESEPYTFSH PNNGDVSSKD TDIPLLNTQF PMEPAE
VCPPSPPTIC SRAPTAKLAT EEPPPRSPPE
```

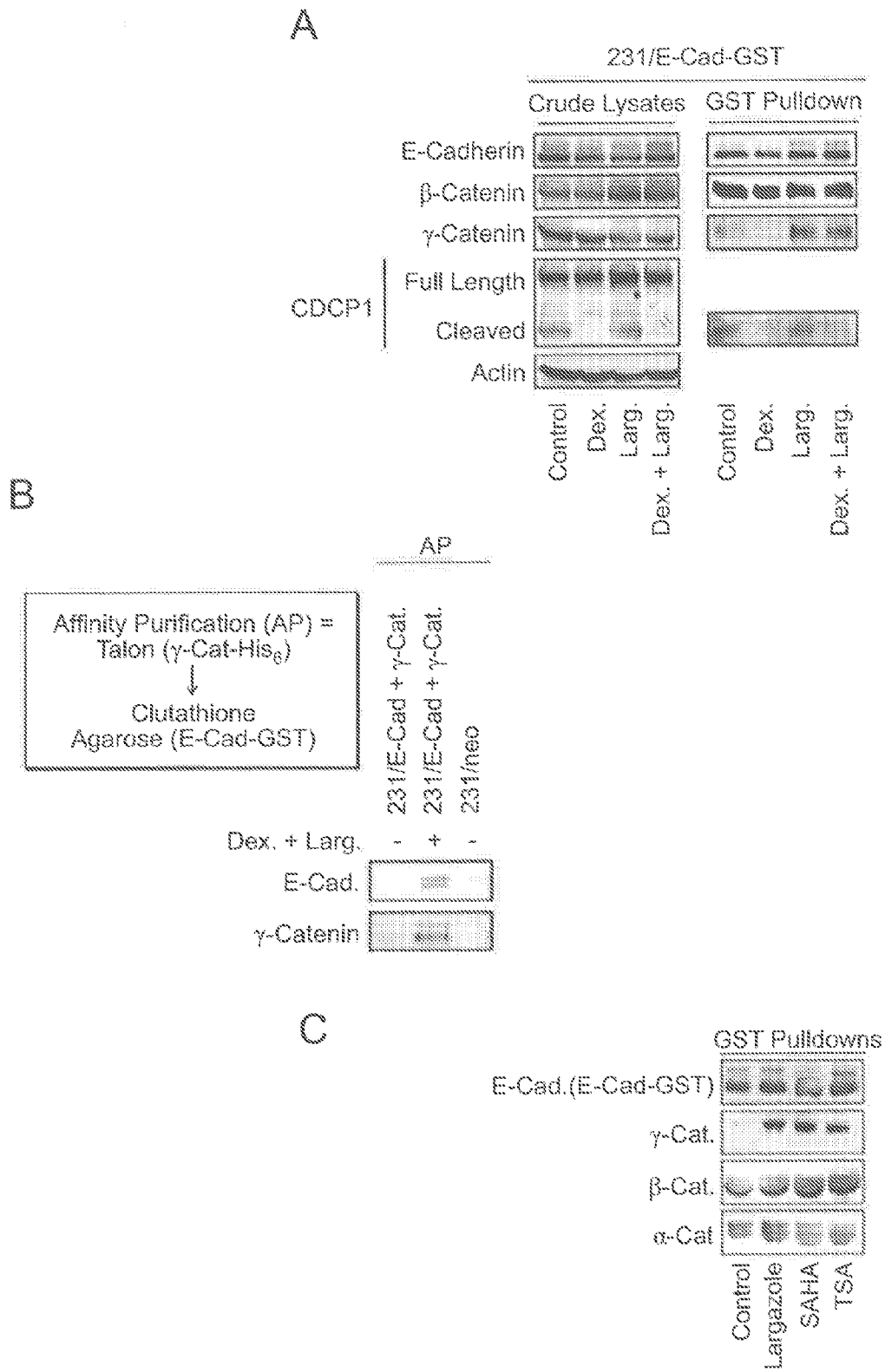

COMBINATION COMPOSITIONS AND METHODS OF TREATMENT

CROSS REFERENCE TO RELATED APPLICATIONS

This application is the U.S. National Stage, pursuant to 35 U.S.C. §371, of U.S. International Application No. PCT/US2012/068479, filed Dec. 7, 2012, designating the United States and published on Jun. 13, 2013 as Publication WO 2013/086344, which claims priority to U.S. Application No. 61/569,057, filed Dec. 9, 2011, the entire contents of which are incorporated herein by reference.

STATEMENT OF RIGHTS TO INVENTIONS MADE UNDER FEDERALLY SPONSORED RESEARCH

This invention was made with government support under Grant No. R01CA138544, awarded by the National Institutes of Health. The government has certain rights in the invention.

BACKGROUND

Basal-like breast tumors are largely overlapping with the triple-negative subtype defined by the absence of Estrogen Receptor and Progesterone Receptor expression, and Her2 overexpression, and tend to be locally invasive and recur at high frequency (Meyers et al 2011, Pazaiti and Fentiman 2011). Results from animal models and the study of human cancers suggest that E-Cadherin functions as a tumor suppressor and an invasion suppressor (Cowin et al 2005). E-Cadherin is often absent or nonfunctional in invasive breast cancers and this is commonly attributed to epigenetic silencing of the E-Cadherin gene, Cdh1 (Jeanes et al 2008). Therefore, efforts have been directed toward reactivating E-Cadherin expression in cancers (Ou et al 2007, Papageorgis et al 2010). However, data also indicate that E-Cadherin is expressed in some invasive breast cancers where it is mislocalized to cytoplasmic vesicles (Corsino et al 2008, Facina et al 2010). Thus, reinstating E-Cadherin expression may not restore its tumor and invasion suppressive actions unless the posttranslational mechanisms that nullify E-Cadherin function in cancers are also blocked.

E-Cadherin is a homophilic cell-cell adhesion molecule whose extracellular domain binds to the extracellular domain of E-Cadherin on adjacent cells and whose cytoplasmic domain binds a number of proteins including p120$^{ctn}$, β-Catenin, and γ-Catenin, also referred to as Junctional Plakoglobin. The latter two proteins bind α-Catenin, which is thought to either directly or indirectly couple the E-Cadherin complex with the Actin cytoskeleton. These multiprotein E-Cadherin-containing complexes play a critical physical role in mediating the formation of adherens junctions in epithelial tissues (Baum and Georgiou 2011), and serve to control the activity of several complex components that also function as transcriptional regulators (Daniel 2007, Heuberger and Birchmeier 2010). As such, mechanisms that converge on E-Cadherin provide an opportunity to address unmet needs in treatment and prevention of disease.

BRIEF SUMMARY OF THE INVENTION

The invention is directed towards compositions and methods of modulating disease and disease processes comprising combinations of active agents, particularly histone deacetylase (HDAC) inhibitor compounds and glucocorticoid compounds.

The invention includes macrocyclic compounds of any of the formulae herein in combination with glucocorticoid compounds, compositions thereof, and methods of modulating disease, disorders, and symptoms thereof in a subject. The combinations are useful in methods of modulating proliferation activity, and methods of treating proliferation disease and disorders, particularly in view of each agent's synergistic action in combination.

In one embodiment, the invention provides a compound according to Formula I:

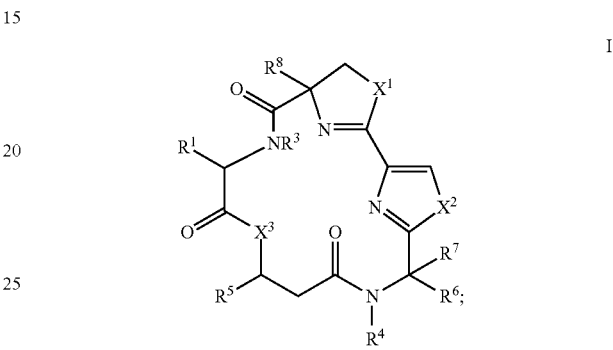

wherein:
each $X^1$ is independently N, O or S;
each $X^2$ is independently N, O or S;
each $X^3$ is independently N, O or S;
each R is independently H or optionally substituted alkyl;
each $R^1$ is independently H, or optionally substituted alkyl;
each $R^2$ is independently —SR, —SC(O)R, —SSR, —N(OH)C(O)R, —C(O)NH(OH), or $SSR^9$;
each $R^3$ is independently H, optionally substituted alkyl, C(O)OR, or C(O)NRR;
each $R^4$ is independently H, optionally substituted alkyl, C(O)OR, or C(O)NRR;
each $R^5$ is independently alkyl or alkenyl, substituted with $R^2$;
each $R^6$ is independently H, or alkyl;
each $R^7$ is independently H, or alkyl;
each $R^8$ is independently H or alkyl;
each $R^9$ is independently

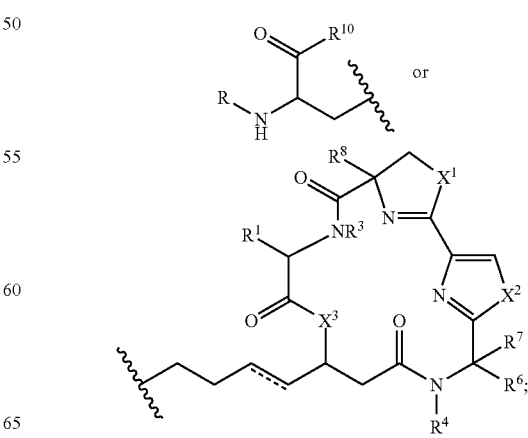

each ═ is independently a single or a double bond;
each $R^{10}$ is independently OR, SR, or NRR; and
each n is independently an integer 0-10, inclusive;
and pharmaceutically acceptable salts, solvates, or hydrates thereof.

Another aspect is a compound of any of the formula herein (e.g., formula (I)) wherein, each $R^5$ is independently

Another aspect is a compound of any of the formulae herein (e.g., formula (I)) wherein, n is 0, 1, 3, 4, 5, 6, 7, 8, 9 or 10.

Another aspect is a compound of any of the formulae herein (e.g., formula (I)) wherein, $X^1$ and $X^2$ are both S.

Another aspect is a compound of any of the formulae herein (e.g., formula (I)) wherein, $X^1$ and $X^2$ are both S and $X^3$ is O.

Another aspect is a compound of any of the formulae herein (e.g., formula (I)) wherein, $R^8$ is methyl.

Another aspect is a compound of any of the formulae herein (e.g., formula (I)) wherein, $R^1$ is isopropyl.

Another aspect is a compound of any of the formulae herein (e.g., formula (I)) wherein, $R^6$ and $R^7$ are both H.

Another aspect is a compound of any of the formulae herein (e.g., formula (I)) wherein, $R^3$ and $R^4$ are both H.

Another aspect is a compound of any of the formulae herein (e.g., formula (I)) wherein, $R^1$ is isopropyl, $R^3$ and $R^4$ are both H, $R^6$ and $R^7$ are both H, and $R^8$ is methyl.

Another aspect is a compound of any of the formulae herein (e.g., formula (I)) wherein, when $X^1$ and $X^2$ are both S and $X^3$ is O, n is 0, 1, 3, 4, 5, 6, 7, 8, 9 or 10.

Another aspect is a compound of any of the formulae herein (e.g., formula (I)) wherein, $R^1$ is isopropyl, $R^3$ and $R^4$ are both H, $R^6$ and $R^7$ are both H, $R^8$ is methyl, $X^1$ and $X^2$ are both S, $X^3$ is O, and n is 0, 1, 2, 3, 4, 5, 6, 7, 8, 9 or 10.

Another aspect is a compound of any of the formulae herein (e.g., formula (I)) wherein, $R^1$ is isopropyl, $R^3$ and $R^4$ are both H, $R^6$ and $R^7$ are both H, $R^8$ is methyl, $X^1$ and $X^2$ are both S, $X^3$ is O, and n is 0, 1, 3, 4, 5, 6, 7, 8, 9 or 10.

Another aspect is a compound of any of the formulae herein (e.g., formula (I)) wherein, when $X^1$ and $X^2$ are both S, $X^3$ is O, each $R^5$ is independently

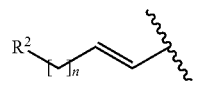

and n is 2, then each $R^2$ is independently —SSR, —N(OH)C(O)R, —C(O)NH(OH), or $SSR^9$.

Another aspect is a compound of any of the formulae herein (e.g., formula (I)) wherein, when $X^1$ and $X^2$ are both S, $X^3$ is O, each $R^5$ is independently

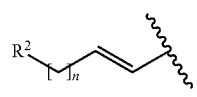

and n is 2, then each $R^2$ is independently —SR or —SC(O)R.

Another aspect is a compound of any of the formula herein (e.g., formula (I)) wherein, each $R^5$ is independently

Another aspect is a compound of any of the formula herein (e.g., formula (I)) wherein, each $R^5$ is independently

Another aspect is a compound of any of the formula herein (e.g., formula (I)) wherein, each $R^2$ is independently —SSR, —N(OH)C(O)R, —C(O)NH(OH), or $SSR^9$.

Another aspect is a compound of any of the formula herein (e.g., formula (I)) wherein, each $R^2$ is independently —SR or —SC(O)R.

Another aspect is a compound of any of the formula herein (e.g., formula (I)) wherein, each $R^8$ is independently H.

Another aspect is a compound of formula Ia (and pharmaceutically acceptable salts, solvates, or hydrates thereof), where all variables (e.g., R, $R^1$, $R^2$, $R^3$, $R^4$, $R^5$, $R^6$, $R^7$, $R^8$, $R^9$, $R^{10}$ and n,) are as defined in formula I:

Formula Ia

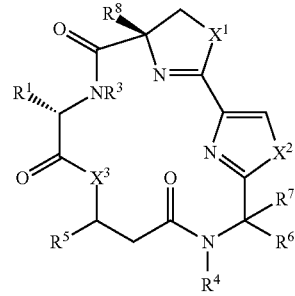

Other embodiments include a compound of any of the formulae herein, wherein $R^3$ and $R^4$ are H; wherein $R^1$ is isopropyl; wherein $R^2$ is —Salkyl; wherein $R^2$ is —SC(O)alkyl; wherein $R^2$ is —SH; or wherein the compound is any of Compounds 1-8 in Table A.

Another aspect is a compound of any of the formula herein (e.g., formula (I)) wherein, each $R^9$ is independently (C)

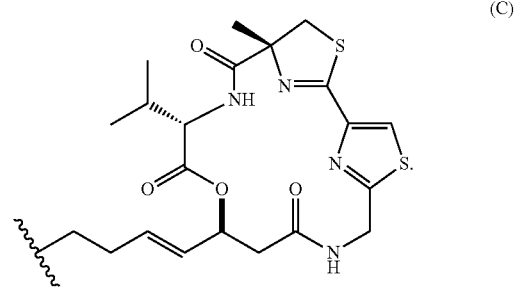 [SMILES: *CC/C=C/[C@@H]1CC(=O)NCc2nc(cs2)C2=N[C@@](C)(CS2)C(=O)N[C@@H](C(C)C)C(=O)O1]

In certain instances, the compounds of the invention are selected from the following of Formula (I) (including formula Ia) having the structure:

TABLE A

| No | R¹ | R² | R³ | R⁴ | R⁵ | R⁶ | R⁷ | R⁸ | R⁹ | R¹⁰ | n | X¹ | X² | X³ |
|----|-----|----|----|----|----|----|----|----|----|-----|---|----|----|----|
| A1 | iPr | —SC(O)Me | H | H | (R⁵'') | H | H | CH₃ | — | — | 4 | S | S | O |
| A2 | iPr | —SC(O)Me | H | H | (R⁵') | H | H | CH₃ | — | — | 3 | S | S | O |
| A3 | iPr | (HO)NC(O)— | H | H | (R⁵') | H | H | CH₃ | — | — | 2 | S | S | O |
| A4 | iPr | MeC(O)NH(OH)— | H | H | (R⁵') | H | H | CH₃ | — | — | 2 | S | S | O |
| A5 | iPr | —SSR⁹ | H | H | (R⁵') | H | H | CH₃ | (B) | OH | 2 | S | S | O |
| A6 | iPr | —SSMe | H | H | (R⁵'') | H | H | CH₃ | — | — | 4 | S | S | O |
| A7 | iPr | —SC(O)Me | H | H | (R⁵'') | H | H | CH₃ | — | — | 4 | S | S | O |
| A8 | iPr | —SSR⁹ | H | H | (R⁵') | H | H | CH₃ | (C) | — | 2 | S | S | O |

In one embodiment, the invention provides a compound according to Formula I:

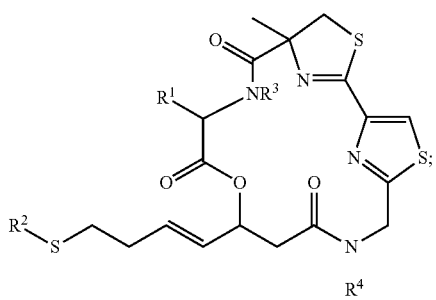

wherein:
each R is independently H or optionally substituted alkyl;
each R' is independently H, or optionally substituted alkyl;
each R² is independently H, optionally substituted alkyl, or C(O)R;
each R³ is independently H, optionally substituted alkyl, C(O)OR, or C(O)NRR;
each R⁴ is independently H, optionally substituted alkyl, C(O)OR, or C(O)NRR;
and pharmaceutically acceptable salts, solvates, or hydrates thereof.

Another aspect is a compound of formula IIa (and pharmaceutically acceptable salts, solvates, or hydrates thereof), where R, R', R², R³, and R⁴ are as defined in formula II:

Formula IIa

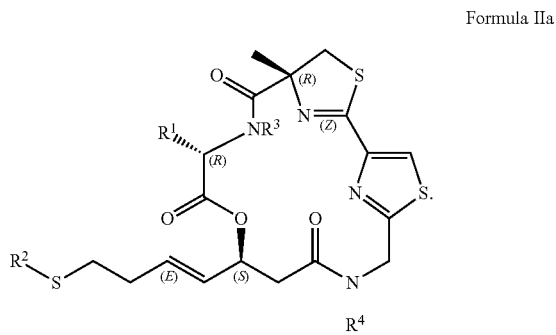

Other embodiments include a compound of any of the formulae herein, wherein R³ and R⁴ are H; wherein R¹ is isopropyl; wherein R² is alkyl; wherein R² is alkylC(O)—; wherein R² is H; wherein the compound is any of Compounds 1-8 in Table B; or wherein the compound is largazole.

In certain instances, the compounds of the invention are selected from the following of Formula (II) (including formula IIa) having the structure:

TABLE B

| Cmpd No. | R¹ | R² | R³ | R⁴ |
|----------|-----|------|----|----|
| B1 | isopropyl | n-heptylC(O)— | H | H |
| B2 | isopropyl | n-heptylC(O)— | H | Me |
| B3 | isopropyl | Me | H | H |
| B4 | isopropyl | n-heptylC(O)— | H | methylC(O)— |
| B5 | isopentyl | n-heptylC(O)— | H | H |
| B6 | ethyl | n-heptylC(O)— | Me | Me |
| B7 | isopropyl | CH₃C(O)— | H | H |
| B8 | isopropyl | H | H | H |

In another aspect the invention provides an HDAC inhibitor compound, that is, a compound thst inhibits an HDAC enzyme (e.g., Class I includes HDAC1, HDAC2, HDAC3, and HDAC8 and have homology to yeast RPD3. HDAC4, HDAC5, HDAC7, and HDAC9 belong to Class II). Examples of such compounds include those of any of the formulae herein (e.g., largazole, largazole derivatives), CI-994, MS-275, BML-210, M-344, NVP-LAQ824, mocetinostat, PXD-101, Tricostatin A (TSA), romidepsin (FK228) and Vorinostat (SAHA).

In another aspect the invention provides a glucocorticoid compound (glucocorticoids), that is, a compound (e.g., a steroid compound) that binds to the glucocorticoid receptor. Examples of such compounds include but are not limited to dexamethasone, prednisone, prednisilone, methyl prednisilone, hydrocortisone, RU-486.

In another aspect, the combination of compounds in the compositions and methods herein is dexamethasone and a compound of any of the formulae herein. In another aspect, the combination of compounds in the compositions and methods herein is dexamethasone and largazole.

In another aspect, the invention provides a pharmaceutical composition comprising the compound of any of the formulae herein (e.g., formula I, Ia, II, IIa), glucocorticoid compound, and a pharmaceutically acceptable carrier.

In other aspects, the invention provides a method of treating a proliferation disease, disorder, or symptom thereof in a subject, comprising administering to the subject a compound of any of the formulae herein (e.g., formula I, Ia, II, IIa), and a glucocorticoid compound. In another aspect, the compound is administered in an amount and under conditions sufficient to ameliorate the proliferation disease, disorder, or symptom thereof in a subject.

In other aspects, the invention provides a method of modulating proliferation activity in a subject, comprising contacting the subject with a compound of any of the formulae herein (e.g., formula I, Ia, II, IIa) and a glucocorticoid compound, in an amount and under conditions sufficient to modulate proliferation activity. In another aspect, the modulation is inhibition.

In one aspect, the invention provides a method of treating a subject suffering from or susceptible to a disorder or disease wherein restoration of E-Cadherin anticance activity modulates the disorder or disease, comprising administering to the subject an effective amount of a compound or pharmaceutical composition of any of the formulae herein (e.g., formula I, Ia, II, IIa), and a glucocorticoid compound.

In another aspect, the invention provides a method of treating a subject suffering from or susceptible to a proliferation disorder or disease, wherein the subject has been identified as in need of treatment for a proliferation disorder or disease, comprising administering to said subject in need thereof, an effective amount of a compound or pharmaceutical composition of any of the formulae herein (e.g., formula I, Ia, II, IIa), and a glucocorticoid compound such that said subject is treated for said disorder.

In another aspect, the invention provides a method of treating a subject suffering from or susceptible to a proliferation disorder or disease, wherein the subject has been identified as in need of treatment for a proliferation-related disorder or disease, comprising administering to said subject in need thereof, an effective amount of a compound or pharmaceutical composition of any of the formulae herein (e.g., formula I, Ia, II, IIa) and a glucocorticoid compound, such that cell proliferation in said subject is modulated (e.g., down regulated).

In another aspect, the invention provides a method of treating diseases, disorders, or symptoms in a subject in need thereof comprising administering to said subject, an effective amount of a compound delineated herein (e.g., Formula I, Ia, II, IIa), and a glucocorticoid compound and pharmaceutically acceptable salts thereof. Such methods are useful for treating proliferation disorders described herein.

In another aspect, the invention provides a method of treating cancer or symptoms thereof in a subject in need thereof comprising administering to said subject, an effective amount of a compound delineated herein (e.g., Formula I, Ia, II, IIa), and a glucocorticoid compound and pharmaceutically acceptable salts thereof. Such methods are useful for treating cancer disorders described herein.

In another aspect, the invention provides a method of treating a subject suffering from or susceptible to E-Cadherin-mediated disease or disease symptoms thereof in a subject in need thereof comprising administering to said subject, an effective amount of a compound delineated herein (e.g., Formula I, Ia, II, IIa), and a glucocorticoid compound and pharmaceutically acceptable salts thereof. Such methods are useful for treating cancer disorders described herein.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

BRIEF DESCRIPTION OF THE DRAWINGS

The present invention is further described below with reference to the following non-limiting examples and with reference to the following figures, in which:

FIG. 6. depicts results showing HDAC inhibitors preferentially increase E-Cadherin interaction with γ-Catenin

DETAILED DESCRIPTION

Definitions

Figure 1:
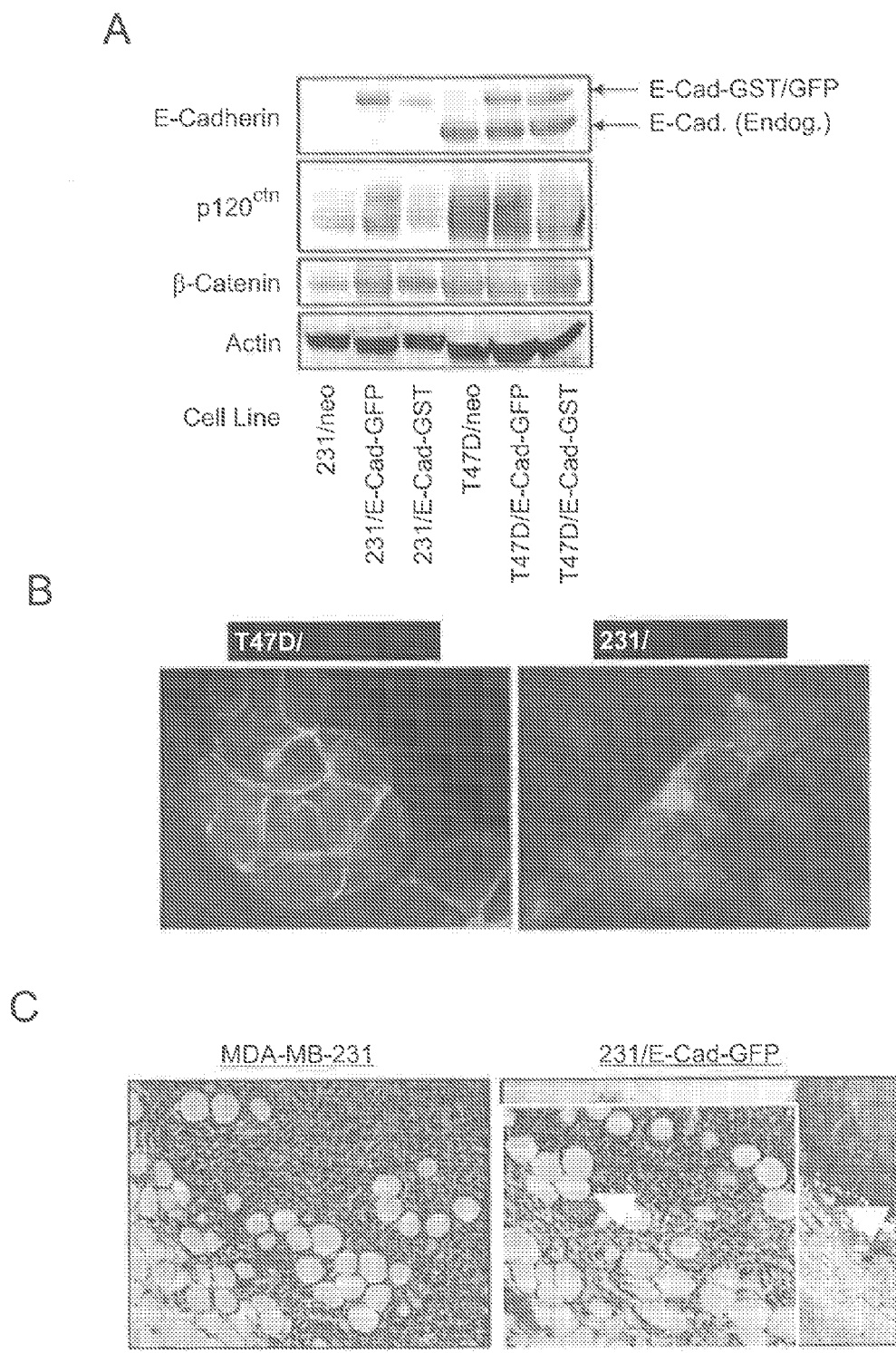
FIG. 1. depicts cellular models for studying E-Cadherin regulation in breast cancer cells in vitro and in vivo.
Figure 1:
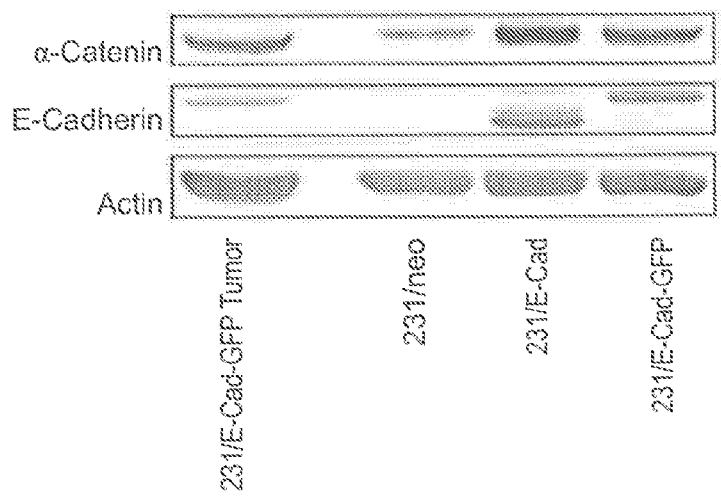

In order that the invention may be more readily understood, certain terms are first defined here for convenience.

As used herein, the term "treating" a disorder encompasses preventing, ameliorating, mitigating and/or managing the disorder and/or conditions that may cause the disorder. The terms "treating" and "treatment" refer to a method of alleviating or abating a disease and/or its attendant symptoms. In accordance with the present invention "treating" includes preventing, blocking, inhibiting, attenuating, protecting against, modulating, reversing the effects of and reducing the occurrence of e.g., the harmful effects of a disorder.

As used herein, "inhibiting" encompasses preventing, reducing and halting progression.

The term "modulate" refers to increases or decreases in the activity of a cell in response to exposure to a compound of the invention.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A "peptide" is a sequence of at least two amino acids. Peptides can consist of short as well as long amino acid sequences, including proteins.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "protein" refers to series of amino acid residues connected one to the other by peptide bonds between the alpha-amino and carboxy groups of adjacent residues.

Amino acids may be referred to herein by either their commonly known three letter symbols or by the one-letter symbols recommended by the IUPAC-IUB Biochemical Nomenclature Commission.

As to amino acid sequences, one of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

Macromolecular structures such as polypeptide structures can be described in terms of various levels of organization. For a general discussion of this organization, see, e.g., Alberts et al., Molecular Biology of the Cell (3rd ed., 1994) and Cantor and Schimmel, Biophysical Chemistry Part I. The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the elastase inhibitor compound are outweighed by the therapeutically beneficial effects.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The term "therapeutically effective amount" refers to that amount of the compound being administered sufficient to prevent development of or alleviate to some extent one or more of the symptoms of the condition or disorder being treated.

A therapeutically effective amount of compound (i.e., an effective dosage) may range from about 0.005 μg/kg to about 200 mg/kg, preferably about 0.1 mg/kg to about 200 mg/kg, more preferably about 10 mg/kg to about 100 mg/kg of body weight. In other embodiments, the therapeutically effect amount may range from about 1.0 μM to about 500 nM. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. In one example, a subject is treated with a compound in the range of between about 0.005 μg/kg to about 200 mg/kg of body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of a compound used for treatment may increase or decrease over the course of a particular treatment.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included. In aspects, the compounds of the invention are prodrugs of any of the formulae herein.

The term "subject" refers to animals such as mammals, including, but not limited to, primates (e.g., humans), cows, sheep, goats, horses, dogs, cats, rabbits, rats, mice and the like. In certain embodiments, the subject is a human.

Furthermore the compounds of the invention include olefins having either geometry: "Z" refers to what is referred to as a "cis" (same side) conformation whereas "E" refers to what is referred to as a "trans" (opposite side) conformation. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl radical.

As used herein, the term "halogen", "hal" or "halo" means —F, —Cl, —Br or —I.

The term "haloalkoxy" refers to an —O-alkyl radical substitued by one or more halo.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thiirenyl, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)CF₃), sulfonates (e.g., mesyl, tosyl), acetamides (e.g., —NHC(O)Me), carbamates (e.g., N(Me)

C(O)Ot-Bu), phosphonates (e.g., —OP(O)(OEt)$_2$), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy.

Compounds of the Invention

Compounds of the invention can be made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis, 2nd Edition*, Carlson R, Ed, 2005; Elsevier Science Ltd.; Jahnisch, K et al, Angew. Chem. Int. Ed. Engl. 2004 43: 406; and references therein). Additional reaction schemes and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. Also embodied are extracts and fractions comprising compounds of the invention. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with an enantiomerically enriched compound, a racemate, or a mixture of diastereomers.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the invention is administered to cells or a subject. In aspects, the compounds are isolated.

Methods of Treatment

The invention is directed towards macrocyclic compounds, and methods of treating disease and disorders using the compounds or compositions thereof delineated herein.

In other aspects, the invention provides a method of treating a subject suffering from or susceptible to a proliferation disorder or disease, wherein the subject has been identified as in need of treatment for a proliferation disorder or disease, comprising administering to said subject in need thereof, an effective amount of a compound or pharmaceutical composition of any of the formulae herein (e.g., formula I, Ia, II, IIa), such that said subject is treated for said disorder. Identifying a subject in need of such treatment can be in the judgment of a subject or a health care professional and can be subjective (e.g. opinion) or objective (e.g. measurable by a test or diagnostic method).

In one aspect, the invention provides a method of modulating the proliferation activity in a subject, comprising contacting the subject with a compound of any of the formulae herein (e.g., formula I, Ia, II, IIa), in an amount and under conditions sufficient to modulate proliferation activity.

In one embodiment, the modulation is inhibition.

In another aspect, the invention provides a method of treating a subject suffering from or susceptible to a proliferation disorder or disease, comprising administering to the subject an effective amount of a compound or pharmaceutical composition of any of the formulae herein (e.g., formula I, Ia, II, IIa).

In other aspects, the invention provides a method of treating a subject suffering from or susceptible to a proliferation disorder or disease, wherein the subject has been identified as in need of treatment for a proliferation disorder or disease, comprising administering to said subject in need thereof, an effective amount of a compound or pharmaceutical composition of any of the formulae herein (e.g., formula I, Ia, II, IIa), such that said subject is treated for said disorder.

In certain embodiments, the invention provides a method as described above, wherein the compound of any of the formulae herein (e.g., formula I, Ia, II, IIa) is largazole.

In certain embodiments, the invention provides a method of treating a disorder, wherein the disorder is cancer, tumor growth, cancer of the colon, breast, bone, brain and others (e.g., osteosarcoma, neuroblastoma, colon adenocarcinoma), comprising administering to said subject in need thereof, an effective amount of a compound delineated herein (e.g., formula I, Ia, II, IIa), and pharmaceutically acceptable salts thereof. Other cancers that may be treated by the compositions and methods of the invention include cardiac cancer (e.g., sarcoma, myxoma, rhabdomyoma, fibroma, lipoma and teratoma); lung cancer (e.g., bronchogenic carcinoma, alveolar carcinoma, bronchial adenoma, sarcoma, lymphoma, chondromatous hamartoma, mesothelioma); various gastrointestinal cancer (e.g., cancers of esophagus, stomach, pancreas, small bowel, and large bowel); genitourinary tract cancer (e.g., kidney, bladder and urethra, prostate, testis; liver cancer (e.g., hepatoma, cholangiocarcinoma, hepatoblastoma, angiosarcoma, hepatocellular adenoma, hemangioma); bone cancer (e.g., osteogenic sarcoma, fibrosarcoma, malignant fibrous histiocytoma, chondrosarcoma, Ewing's sarcoma, malignant lymphoma, cutaneous T-cell lymphoma, multiple myeloma, malignant giant cell tumor chordoma, osteochronfroma, benign chondroma, chondroblastoma, chondromyxofibroma, osteoid osteoma and giant cell tumors); cancers of the nervous system (e.g., of the skull, meninges, brain, and spinal cord); gynecological cancers (e.g., uterus, cervix, ovaries, vulva, vagina); hematologic cancer (e.g., cancers relating to blood, Hodgkin's disease, non-Hodgkin's lymphoma); skin cancer (e.g., malignant melanoma, basal cell carcinoma, squamous cell carcinoma, Karposi's sarcoma, moles dysplastic nevi, lipoma, angioma, dermatofibroma, keloids, psoriasis); and cancers of the adrenal glands (e.g., neuroblastoma). Other diseases and disorders that can be treated include the treatment of inflammatory disorders, neurodegenerative diseases, protozoal and latent viral infections, and (fibro)proliferative disorders.

In another aspect, the invention provides a method of inhibiting histone deacetylase (HDAC) in a subject in need thereof comprising administering to said subject, an effective amount of a compound delineated herein (e.g., formula I, Ia, II, IIa), and pharmaceutically acceptable salts thereof.

In certain embodiments, the subject is a mammal, preferably a primate or human.

In another embodiment, the invention provides a method as described above, wherein the effective amount of the compound delineated herein ranges from about 0.005 µg/kg to about 200 mg/kg. In certain embodiments, the effective amount of the compound of the formulae herein (e.g., formula I, Ia, II, IIa) ranges from about 0.1 mg/kg to about 200 mg/kg. In a further embodiment, the effective amount of compound delineated herein ranges from about 10 mg/kg to 100 mg/kg.

In other embodiments, the invention provides a method as described above wherein the effective amount of the compound delineated herein ranges from about 1.0 µM to about 500 nM. In certain embodiments, the effective amount ranges from about 10.0 µM to about 1000 µM. In another embodiment, the effective amount ranges from about 1.0 nM to about 10 nM.

In another embodiment, the invention provides a method as described above, wherein the effective amount of the glucocorticoid compound ranges from about 0.005 µg/kg to about 200 mg/kg. In certain embodiments, the effective amount of the compound delineated herein ranges from about 0.1 mg/kg to about 200 mg/kg. In a further embodiment, the effective amount of compound of formula I ranges from about 10 mg/kg to 100 mg/kg.

In another embodiment, the invention provides a method as described above, wherein the compound delineated herein is administered intravenously, intramuscularly, subcutaneously, intracerebroventricularly, orally or topically.

In other embodiments, the invention provides a method as described above, wherein the compound delineated herein is administered alone or in combination with one or more other therapeutics. In a further embodiment, the additional therapeutic agent is a anti-cancer agent.

Another object of the present invention is the use of a compound as described herein (e.g., of any formulae herein) in the manufacture of a medicament for use in the treatment of a proliferation disorder or disease. Another object of the present invention is the use of a compound as described herein (e.g., of any formulae herein) for use in the treatment of a proliferation disorder or disease.

Pharmaceutical Compositions

In one aspect, the invention provides a pharmaceutical composition comprising the compound of any of the formulae herein (e.g., formula I, Ia, II, IIa), a glucocorticoid compound, and a pharmaceutically acceptable carrier.

In one embodiment, the invention provides a pharmaceutical composition wherein the compound of any of the formulae herein (e.g., formula I, Ia, II, IIa) is largazole, and a pharmaceutically acceptable carrier.

In another embodiment, the invention provides a pharmaceutical composition further comprising an additional therapeutic agent. In a further embodiment, the additional therapeutic agent is an anti-cancer agent.

In one aspect, the invention provides a kit comprising an effective amount of a compound of any of the formulae herein (e.g., formula I, Ia, II, IIa) and a glucocorticoid compound, in unit dosage form, together with instructions for administering the compound to a subject suffering from or susceptible to a proliferation disease or disorder, including any of those specifically listed herein.

In one aspect, the invention provides a kit comprising an effective amount of a compound of any of the formulae herein (e.g., formula I, Ia, II, IIa) and a glucocorticoid compound, in unit dosage form, together with instructions for administering the compound to a subject suffering from or susceptible to a proliferation disease or disorder.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention also provides a pharmaceutical composition, comprising an effective amount a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic (or unacceptably toxic) to the patient.

In use, at least one compound according to the present invention is administered in a pharmaceutically effective amount to a subject in need thereof in a pharmaceutical carrier by intravenous, intramuscular, subcutaneous, or intracerebroventricular injection or by oral administration or topical application. In accordance with the present invention, a compound of the invention may be administered alone or in conjunction with a second, different therapeutic. By "in conjunction with" is meant together, substantially simultaneously or sequentially. In one embodiment, a compound of the invention is administered acutely. The compound of the invention may therefore be administered for a short course of treatment, such as for about 1 day to about 1 week. In another embodiment, the compound of the invention may be administered over a longer period of time to ameliorate chronic disorders, such as, for example, for about one week to several months depending upon the condition to be treated.

By "pharmaceutically effective amount" as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific organozinc compound employed. For example, a therapeutically effective amount of a compound of the invention administered to a child or a neonate will be reduced proportionately in accordance with sound medical judgment. The effective amount of a compound of the invention will thus be the minimum amount which will provide the desired effect.

A decided practical advantage of the present invention is that the compound may be administered in a convenient manner such as by intravenous, intramuscular, subcutaneous, oral or intra-cerebroventricular injection routes or by topical application, such as in creams or gels. Depending on the route of administration, the active ingredients which comprise a compound of the invention may be required to be coated in a material to protect the compound from the action of enzymes, acids and other natural conditions which may inactivate the compound. In order to administer a compound of the invention by other than parenteral administration, the compound can be coated by, or administered with, a material to prevent inactivation.

The compound may be administered parenterally or intraperitoneally. Dispersions can also be prepared, for example, in glycerol, liquid polyethylene glycols, and mixtures thereof, and in oils.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage. The carrier can be a solvent or dispersion medium containing, for example, water, DMSO, ethanol, polyol (for example, glycerol, propylene glycol, liquid polyethylene glycol, and the like), suitable mixtures thereof and vegetable oils. The proper fluidity can be maintained, for example, by the use of a coating such as lecithin, by the maintenance of the required particle size in the case of dispersion. In many cases it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the compound of the invention in the required amount in the appropriate solvent with various of the other ingredients enumerated above, as required, followed by filtered sterilization. Generally, dispersions are prepared by incorporating the various sterilized compounds into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yields a powder of the active ingredient plus any additional desired ingredient from previously sterile-filtered solution thereof.

For oral therapeutic administration, the compound may be incorporated with excipients and used in the form of ingestible tablets, buccal tablets, troches, capsules, elixirs, suspensions, syrups, wafers, and the like. Compositions or preparations according to the present invention are prepared so that an oral dosage unit form contains compound concentration sufficient to treat a disorder in a subject.

Some examples of substances which can serve as pharmaceutical carriers are sugars, such as lactose, glucose and sucrose; starches such as corn starch and potato starch; cellulose and its derivatives such as sodium carboxymethylcellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of *theobroma*; polyols such as propylene glycol, glycerine, sorbitol, mannitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tableting agents, stabilizers, anti-oxidants and preservatives, can also be present.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

EXAMPLES

The present invention will now be demonstrated using specific examples that are not to be construed as limiting. Definitions of variables in the structures in schemes herein are commensurate with those of corresponding positions in the formulae delineated herein.

General Experimental Procedures

Materials and Methods
Preparation of Cell Extracts and Immunoblot Analysis—
Cells were grown in Dulbecco's Modified Essential Medium (SH30003.03; Hyclone Laboratories Inc., Logan, Utah) supplemented with 10% Fetal Bovine Serum (10% FBS-DMEM) in a humidified 37° C. incubator with 5% $CO_2$. Cell extraction was performed as described previously (Law et al 2002) using buffer containing 1% Triton X100, 20 mM HEPES (pH 7.4), 1 mM EDTA, 1 mM EGTA, 0.1% β-mercaptoethanol, 5% glycerol, 10 nM microcystin, 200 μM $Na_3VO_4$, and 40 mM $Na_2H_2P_2O_7$. Immunoblots were probed with antibodies specific for Actin (sc-1616R), β-Catenin (sc-7199), N-Cadherin (sc-7939), P-Cadherin (sc-7893), phosphotyrosine (sc-7020 (PY99)) and γ-Catenin (sc-7900) purchased from Santa Cruz Biotechnology Inc., Santa Cruz, Calif.; antibodies specific for α-Catenin (#3236) and CDCP1 (#4115) from, Cell Signaling Technology, Danvers, Mass.; antibody specific for phosphorylated tyrosine (Cat. 05-321 (4G10)) from Millipore, Billerica, Mass.; antibodies specific for E-Cadherin (610182) and p120$^{ctn}$ (610133) from BD Biosciences, Franklin Lake, N.J.; and an antibody specific for γ-Catenin (138500) from Invitrogen, Carlsbad, Calif. Cells were treated with Dexamethasone (S1322; Selleck Chemicals, Houston, Tex.), RU486 (10006317; Cayman Chemical, Ann Arbor, Mich.), Vorinostat (S1047; Selleck Chemicals), or Trichostatin A (T8552, Sigma-Aldrich) at the doses and for the durations indicated in the figure legends. Largazole was synthesized as described previously (Ying et al 2008b).

Fluorescence and Immunofluorescence Microscopy—
Fluorescence and immunofluorescence microscopy were performed essentially as described previously (Corsino et al 2008) employing antibodies to E-Cadherin (610182; BD Bioscience) and γ-Catenin (138500; Invitrogen, Carlsbad, Calif.).

In Vitro Invasion Assays—
Invasion assays were performed using BD BioCoat Matrigel Invasion Chambers (Cat. 354481) according to the manufacturer's instructions. Cells for invasion assays were treated for 72 hrs with Dexamethasone, Largazole, or Dexamethasone+Largazole and removed from the flasks with Trypsin/EDTA and washed twice in 10% FBS-DMEM to remove traces of the Trypsin used to detach the cells from the culture flasks. The cells were counted, diluted, and added to the upper chambers of the apparatus in the continued presence of the treatment solutions in medium containing 0.2% FBS. The lower chambers also contained drug treatments, but were supplemented with 10% FBS. Invasion was allowed to proceed for 48 hrs. Non-invaded cells were removed and invaded cells were stained with crystal violet. The assays were performed in triplicate and for each replicate cells were counted in five random microscope fields. Experiments were repeated three times with similar results.

Orthotopic Tumor Studies—
Cultured tumor cells were removed from the culture flasks with Trypsin/EDTA, washed twice with 10% FBS-DMEM, twice with sterile saline, and counted. Cells ($2\times10^6$) were injected into the right inguinal (#4) mammary fat pad of 3-5 week old female athymic nude (nu/nu) mice (Charles Rivers International, Inc., Wilmington, Mass.) in 100 μl of sterile saline. For analysis of tumor invasion into the mammary fat pad the animals were sacrificed when the tumors reached 2-3 mm in diameter and the mammary glands were excised, fixed with 4% paraformaldehyde, paraffin embedded, sectioned, and stained with hematoxylin and eosin. Tumor extracts for immunoblot analysis were prepared as described previously (Law et al 2006). All studies involving animals were approved by the University of Florida Institutional Animal Care and Use Committee.

Design of Viral cDNA Expression Constructs and Adenovirus Construction—
Construction of γ-Catenin constructs: Human γ-Catenin was PCR amplified from the Addgene (Cambridge, Mass.) plasmid 16827 encoding γ-Catenin in pcDNA3 to add a 5' BamHI site, a 3' $His_6$ tag, and a 3' EcoRI site to γ-Catenin. The primers used to amplify γ-Catenin were as follows: 5'-TTTTGGATCCATGGAGGTGATGAACCTGATG-3' and 5'-TTTTGAATTCCTAATGATGATGATGATGATGGGCCAGCATGTGGTCTGC-3'. PCR amplified γ-Catenin-$His_6$ was subsequently digested with BamHI and EcoRI and cloned into the corresponding restriction sites of pBabe-Puro (Addgene plasmid 1764; (Morgenstern and Land 1990)).

To generate adenovirus expressing γ-Catenin-$His_6$, γ-Catenin-$His_6$ was excised from the γ-Catenin-$His_6$/pBabe-Puro vector with BamHI and SalI and cloned into the BglII and SalI sites of pShuttle-CMV (He et al 1998). The γ-Catenin-$His_6$/pShuttle-CMV vector was recombined with pAdEasyl in BJ5183 cells using an electroporator set at 200 Ohms, 25 mF, and 2.5 kV. Recombinant γ-Catenin-$His_6$/pAdEasyl linearized with Pac I was transfected into HEK 293A cells using Lipofectamine (Invitrogen, Carlsbad, Calif.), according to manufacturer's instructions. Adenovirus expressing γ-Catenin-$His_6$ was subsequently amplified in HEK 293 cells.

Construction of E-Cadherin constructs: QuikChange site-directed mutagenesis (Agilant, Santa Clara, Calif.) was used to add BglII and SpeI sites 5' to the stop codon of the cDNA encoding human E-Cadherin in the E-Cadherin/pMS plasmid using the following primers: 5'-GCTGACATGTACG-GAGGCGGCGAGGACGACAGATCTAAGCT-TACTAGTTA
GGGGACGCTAGGTACCGATATCGGCCGGTCCGGC-CTAG-3' and 5'-CTAGGCCGGACCGGCCGATATCGG-TACCTAGCGTCCCCTAACTAGTAAGC TTAGATCT-GTCGTCCTCGCCGCCTCCGTACATGTCAGC-3'. The presence of BglII and SpeI sites was confirmed by restriction digests. cDNA encoding Green Fluorescent Protein (GFP) from *Aequorea coerulescens* (AcGFP1) was subsequently PCR amplified to add a 5' BamHI site and a 3' SpeI site to GFP. Oligonucleotides used to amplify GFP are as follows: 5'-TTTTGGATCCGTGAGCAAGGGCGCCCGAG-3' and 5'-TTTTACTAGTCTTGTACAGCTCATCCATGCC-3'.
cDNA encoding Glutathione S-Transferase (GST) from *Schistosoma japonicum* was also PCR amplified to add a 5' BamH1 site and a 3' SpeI site. Oligonucleotides used to amplify GST were as follows: 5'-TTTTGGATCCATGGC-CCCTATACTAGGTTAT-3' and 5'-TTTTACTAGTACGCG-GAACCAGATCCGATTTTGG-3'. PCR amplified GFP and GST were digested with BamHI and SpeI and ligated into the BglII and SpeI sites of E-Cadherin/pMS. Thus, GFP and GST were cloned 3' to the coding sequence of E-Cadherin in E-Cadherin/pMS. E-Cadherin-GFP and E-Cadherin-GST coding regions were subsequently excised from the pMS vector using SfiI and SgfI and cloned into the corresponding sites in LZRS. The LZRS and E-Cadherin/pMS plasmids (Ireton et al 2002, Kinsella and Nolan 1996) were generously provided by Dr. Al Reynolds (Vanderbilt University, Nashville, Tenn.).

Construction of Stable Cell Lines—

Viruses produced using the vectors encoding E-Cadherin and γ-Catenin-His$_6$ described above were packaged using *Phoenix* cells (Swift et al 2001) and the viruses were used to infect the target cell lines as described previously (Law et al 2002). Cells infected with the E-Cadherin vectors were selected with 2 mg/ml G418, and cells infected with the γ-Catenin-His$_6$ retroviral vector were selected with 5 μg/ml Puromycin. To produce stable lines doubly transduced with E-Cadherin and γ-Catenin, the lines expressing the E-Cadherin constructs were infected with the γ-Catenin-His$_6$ retroviral vector and the resulting cells were selected with 2 mg/ml G418+5 μg/ml Puromycin.

Affinity Purification of E-Cadherin Complexes and Immunoprecipitation—

Cells were subjected to hypotonic lysis and membrane fractions were isolated by centrifugation for one hour at 100,000×g. The pellet was solubilized by sonication in buffer containing 2% Triton X100, 20 mM HEPES (pH 7.4), 1 mM EDTA, 1 mM EGTA, 0.1% β-mercaptoethanol, 5% glycerol, 10 nM microcystin, 200 μM Na$_3$VO$_4$, and 40 mM Na$_2$H$_2$P$_2$O$_7$. The membrane extract was centrifuged for one hour at 100,000×g, and the supernatant was used for E-Cadherin purifications. Complexes containing E-Cad-GST were isolated using glutathione-agarose (G4510; Sigma-Aldrich, St. Louis, Mo.), washed, and either eluted with 5 mM glutathione or eluted by boiling in SDS-PAGE sample buffer. In sequential purifications involving γ-Catenin-His$_6$ and E-Cad-GST proteins expressed in the same cells, TALON (635503; Clontech Laboratories, Inc., Mountain View, Calif.) resin purifications were performed as described previously (Chytil et al 2004), and the 400 mM imidazole eluents were diluted ten-fold and purified using glutathione-agarose, followed by elution with 5 mM glutathione. Sequential affinity purification experiments were performed using cells stably expressing both E-Cad-GST and γ-Catenin-His$_6$, or were carried out in 231/E-Cad-GST cells that had been infected with an adenovirus encoding γ-Catenin-His$_6$ or an adenovirus encoding GFP as a control. The affinity purifications performed using either strategy produced identical results in terms of the observed effects of Dexamethasone and Largazole on E-Cadherin complexes. Immunoprecipitations were performed as described previously (Law et al 2002) using 2 mg of total protein extract per sample and 4 μg of antibody per sample. Immunoprecipitates prepared using antibodies to E-Cadherin (610182; BD Biosciences) or GST (sc-459; Santa Cruz Biotechnology Inc.) were isolated with 35 μl per sample Protein G-Sepharose (10-1242; Invitrogen), washed, and eluted by boiling in SDS-PAGE sample buffer.

Identification of CDCP1 by Mass Spectrometry—

Tyrosine phosphorylated proteins were isolated by immunoprecipitation as described above using the 4G10 antiphosphotyrosine antibody (05-321; Millipore) and the proteins were visualized by staining with colloidal coomassie (LC6025; Invitrogen). A protein doublet of approximately 80 kDa that was present in samples derived from vehicle (DMSO) treated cells, but not in cells treated with 100 nM Dexamethasone for 72 h, was excised and digested with trypsin as previously described (Sheffield et al 2006). The tryptic peptides were separated on an LC Packing® C18 Pep Map HPLC column and LC-MS/MS analysis was carried out on a hybrid quadrupole-TOF mass spectrometer (QSTAR Elite, AB Sciex Inc., Framingham, Mass.).

Tandem mass spectra were extracted by ABI Analyst version 1.1. All MS/MS samples were analyzed using Mascot (Matrix Science, London, UK; version 2.0.01). Peptide identifications were accepted if they could be established at greater than 95.0% probability as specified by the Peptide Prophet algorithm (Keller et al 2002). Protein identifications were accepted if they could be established at greater than 99.0% probability and contain at least two identified unique peptides. Protein probabilities were assigned by the Protein Prophet algorithm (Nesvizhskii et al 2003).

Proteomic Comparison of E-Cadherin Complexes Between Invasive and Noninvasive Cancer Cell Lines by iTRAQ Analysis—

The two samples being compared represented equal amounts of E-Cadherin complexes isolated from either T47D or MDA-MB-231 cells stably expressing the E-Cadherin-Glutathione S-Transferase (E-Cad-GST) fusion protein, by glutathione-agarose affinity chromatography. The samples were reduced, alkylated, trypsin-digested and labeled using the iTRAQ Reagents Multiplex kit according to manufacturer's instructions (Applied Biosystems, Foster City, Calif.). The labeled peptides were separated on a MacroSpin Vydac C18 reverse phase minicolumn (The Nestgroup Inc., USA). The eluates were dried down and dissolved in strong cation exchange (SCX) solvent A (25% v/v acetonitrile, 10 mM ammonium formate, pH 2.8). The peptides were fractionated on an Agilent HPLC system 1100 using a polysulfoethyl A column (2.1×100 mm, 5 μm, 300 Å, PolyLC, Columbia, Md.).

Each SCX fraction was lyophilized and redissolved in Solvent A (3% acetonitrile v/v, 0.1% acetic acid v/v) plus 0.01% trifluoroacetic acid. The peptides were loaded onto a C18 capillary trap cartridge (LC Packings) and then separated on a 15-cm nanoflow C18 column (PepMap 75 μm id, 3 μmm, 100 A) (LC Packings). The HPLC instrument and the quadrupole time-of-flight (QSTAR Elite) MS system were the same as previously described (Zhu et al 2010). The instrument was operated in an information-dependent data acquisition mode where a MS scan followed by three MS/MS scans of four highest abundance peptide ions were acquired in each cycle.

The MS/MS Data was processed by a thorough search considering biological modifications against an IPI human database using the Paragon algorithm (Shilov et al., 2007) of ProteinPilot v4.0 software suite (Applied Biosystems, USA).

For protein relative quantification using iTRAQ, only MS/MS spectra unique to a particular protein and where the sum of the signal-to-noise ratio for all of the peak pairs greater than nine were used for quantification (software default settings, Applied Biosystems, USA). The mean, standard deviation, and p values to estimate statistical significance of the protein changes were calculated by Pro-Group.

Compounds such as romidepsin (FK228), Vorinostat (SAHA), dexamethasone, RU-486, prednisone, prednisilone, methyl prednisilone, hydrocortisone are available from commercial sources.

A sample of *Symploca* sp. was collected from Key Largo, Florida Keys and extracted with organic solvents. The resulting cytotoxic crude extract was subjected to bioassay-guided fractionation by solvent partition, silica gel chromatography and reversed-phase HPLC to yield largazole (L) as a colorless, amorphous solid $\{[\alpha]^{20}_D+22$ (c 0.1, MeOH)$\}$.

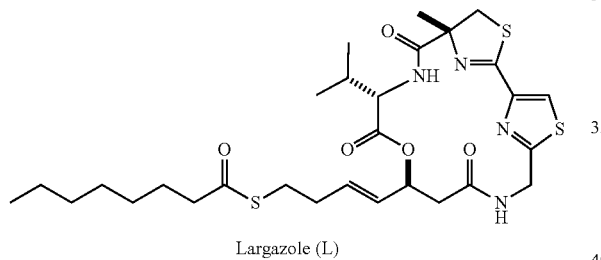

Largazole (L)

$^1$H and $^{13}$C NMR data coupled with a [M+H]$^+$ peak at m/z 623.2397 in the HR-ESI/APCI-MS of (L) suggested a molecular formula of $C_{29}H_{42}N_4O_5S_3$ (calcd for $C_{29}H_{43}N_4O_5S_3$, 623.2396). See, Table 1.

Largazole (L) can be used as a starting point for derivatization to provide largazole derivatives of formula (I), and other formulae herein using standard synthetic chemistry procedures and reagents kown in the art, including those specifically delineated herein. See, e.g., Scheme I.

Scheme I

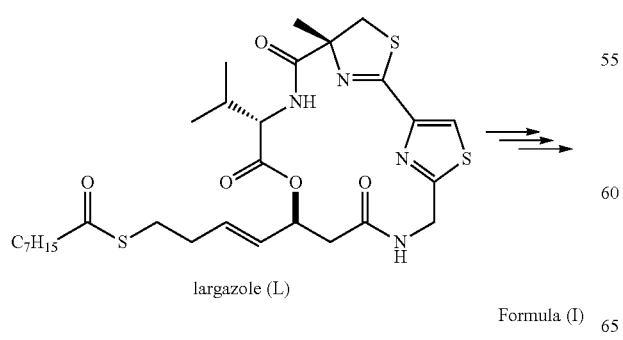

Formula (I)

Compounds of the invention can be made by means known in the art of organic synthesis. For example, those such as described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof are representative and instructive. Methods for optimizing reaction conditions, if necessary minimizing competing by-products, are known in the art.

For example, largazole (L) can be hydrolyzed under standard conditions (e.g., aminolysis (NH$_3$, acetonitrile or methanol) to provide the mercaptan (A), which can them be coupled under standard conditions (e.g., oxidation, H$_2$O$_2$, or DEAD, and the like) with another mercaptan (or second molecule of the same mercaptan for symmetrical disulfides) to provde disulfide (B). See, e.g., Scheme II.

Scheme II

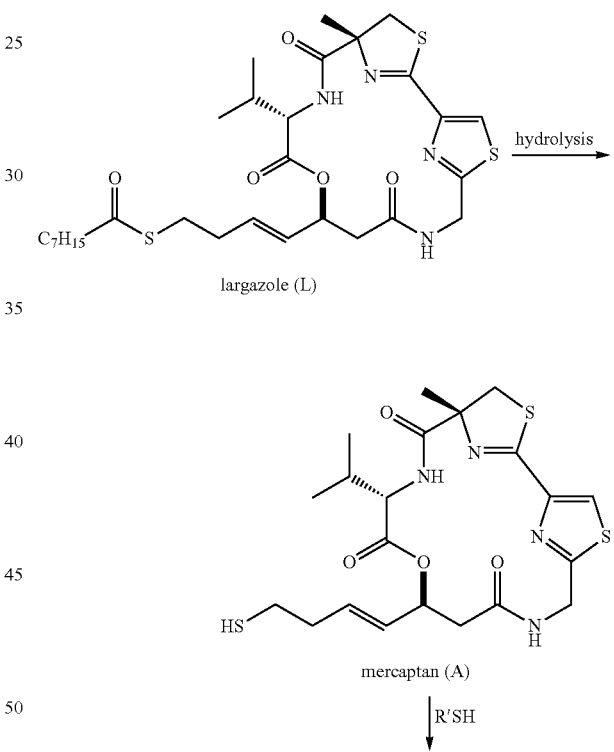

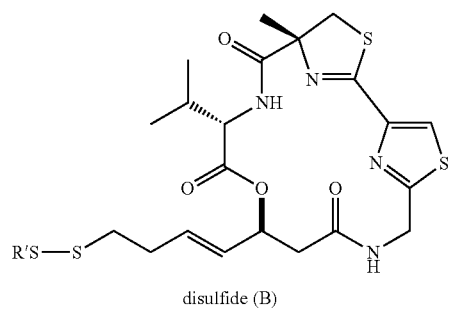

disulfide (B)

-continued

R' = e.g., alkyl, alkenyl, alkynyl, cycloalkyl, cyclyl, heteroalkyl, aryl, heteroaryl, or (C), each optionally substituted

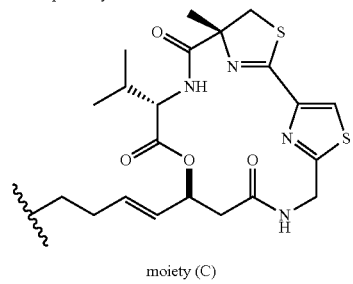

moiety (C)

Example 1

E-Cadherin is Nonfunctional in Invasive Breast Cancer Cells Even when it is Expressed at High Levels MDA-MB-231 and T47D cell lines were engineered to stably express E-Cadherin fused with either GFP or GST, and the resulting cell lines were analyzed by immunoblot in comparison with the corresponding vector control cell lines transduced with the empty retroviral vector encoding the Neomycin resistance gene (FIG. 1A). Fluorescence microscopy indicated that E-Cad-GFP is localized to cell-cell junctions in the T47D cells, but distributed throughout the cytoplasm in MDA-MB-231 cells (FIG. 1B). MDA-MB-231 cells stably expressing E-Cad-GFP exhibited the same properties as the parental MDA-MB-231 cells when injected into the mammary fat pads of athymic nude mice, including the formation of tumors that lack a defined tumor-stroma boundary and invade into the adjacent mammary gland (FIG. 1C). This result indicates that E-Cad-GFP expression does not block tumor invasion in vivo. Immunoblot analysis of tumors derived from the 231/E-Cad-GFP cells indicated that E-Cad-GFP expression was retained during tumor formation and growth (FIG. 1D). Together, these results indicate that E-Cadherin expressed in the invasive MDA-MB-231 cells does not localize to cell-cell contacts in vitro and does not block invasion in vivo. This demonstrates that in addition to low E-Cadherin expression levels, E-Cadherin function is suppressed in MDA-MB-231 cells through posttranslational mechanisms.

Example 2

E-Cadherin Forms Complexes with Adherens Junction Components in Invasive Breast Cancer Cells, but with an Altered Ratio of β-Catenin Versus γ-Catenin Binding E-Cadherin-GST complexes were isolated from the membrane fractions of the T47D/E-GST and 231/E-GST cell lines by affinity chromatography using glutathione-agarose and analyzed by SDS-PAGE/silver stain (FIG. 2A, left panel) and proteomics using iTRAQ labeling. The proteomics results were verified by immunoblot (FIG. 2A, right panel). E-Cadherin-containing complexes were similar between the two cell lines with the exception that the ratio of γ-Catenin to β-Catenin bound with E-Cadherin was significantly higher in the T47D cells as compared with the MDA-MB-231 cells. This difference may be partly explained by the relatively high levels of γ-Catenin expression in the T47D cells as compared with the MDA-MB-231 cells. Similar results were obtained if E-Cadherin complexes were isolated by immunoprecipitation using antibodies to E-Cadherin or GST (FIG. 2B). These findings suggested that the relatively low level of γ-Catenin expression in MDA-MB-231 cells might be responsible for the localization of E-Cadherin to the cytoplasm. To test this hypothesis, we generated MDA-MB-231 cell lines stably expressing hexahistidine tagged γ-catenin (γ-Catenin-His$_6$), or expressing γ-Catenin-His$_6$ in combination with E-Cadherin, E-Cad-GFP, or E-Cad-GST. Immunoblot analysis indicated that each of the proteins was expressed as expected (FIG. 2C). Interestingly, α-Catenin was expressed at very low levels in the control 231/neo cells transduced with the empty retroviral vector as compared with the cell lines overexpressing E-Cadherin or γ-Catenin either separately or together. However, despite the increased expression of α-Catenin and γ-Catenin in the doubly transduced stable cell lines, the resulting cell lines exhibited a mesenchymal morphology similar to that of the parental MDA-MB-231 cells and did not form colonies when grown in culture, indicating a lack of cell-cell adhesion (not shown). Together, the results in FIGS. 1 and 2 suggest that the diminished E-Cadherin function in the MDA-MB-231 cells is not simply due to decreased E-Cadherin, γ-Catenin, or α-Catenin expression. We hypothesized that additional posttranslational mechanisms may be operative that prevent proper E-Cadherin membrane localization and function in MDA-MB-231 cells, and that it may be possible to antagonize these mechanisms pharmacologically.

Example 3

Dexamethasone and Largazole Cooperate to Restore the Formation of Adherens Junctions in Invasive Breast Cancer Cells and to Block their Invasion The 231/E-GFP cell line was treated with a series of small molecule signaling agonists and antagonists to identify compounds that modulate E-Cadherin localization within the cell. Of the agents screened, the glucocorticoid Dexamethasone (Dex) and the highly potent HDAC inhibitor Largazole (Larg) (Taori et al 2008, Ying et al 2008b) modestly increased E-Cadherin localization to the cell-cell periphery, and combination of the two drugs caused a more complete E-Cadherin junctional localization than either agent alone (FIG. 3A). Changes in E-Cadherin localization partially overlapped with changes in γ-Catenin localization. In vitro invasion assays were performed to determine the respective effects of E-Cadherin expression and Dex.+Larg. treatment on the invasiveness of MDA-MB-231 cells. The results demonstrated that E-Cadherin expression and Dex.+Larg. treatment each decreased invasiveness and that combined E-Cadherin expression and Dex.+Larg. treatment reduced invasion more than either manipulation alone (FIG. 3B). This suggests that although Dex.+Larg. treatment induces membrane localization of E-Cadherin, this treatment also suppresses invasion through additional mechanisms.

Similar experiments were carried out in the BT549 invasive basal-like human breast cancer cell line that expresses a moderate level (see FIG. 5B, below) of endogenous wild type E-Cadherin (Lombaerts et al 2006). Dex. and Larg. cooperated to increase the junctional localization of endogenous E-Cadherin in BT549 cells (FIG. 3C). These effects were partially reversed by the glucocorticoid receptor antagonist RU486. Dexamethasone and Largazole each suppressed the invasion of BT549 cells in vitro, and combination of the two agents diminished invasion to a greater extent than either one alone (FIG. 3D). The mechanisms by which Dexamethasone and Largazole influence E-Cadherin localization and function are unknown. Therefore the cellular effects of each of these agents were further explored.

Example 4

Dexamethasone+Largazole Prevents the Cleavage of CDCP1

Dissolution of adherens junctions can be caused by the activation of tyrosine kinases such as c-Src or c-Met, and this is associated with tyrosine phosphorylation of adherens junctions components such as β-Catenin and E-Cadherin (Behrens et al 1993, Hiscox and Jiang 1999, Matsuyoshi et al 1992). Therefore we examined whether Dexamethasone treatment causes changes in the patterns of cellular protein tyrosine phosphorylation. Immunoblot analysis of MDA-MB-231 cell lysates with two different anti-phosphotyrosine antibodies revealed a band of approximately 80 kDa that vanished upon treatment of the cells with Dex.+Larg. (FIG. 4A), while the intensity of the other bands was unaffected. The same extracts were immunoprecipitated with an anti-phosphotyrosine antibody and the immunoprecipitates were resolved by SDS-PAGE and visualized by colloidal coomassie staining. A doublet in the vicinity of the 80 kDa molecular weight marker was digested with trypsin and identified by mass spectrometry. Ten of the peptides identified were from the 130 kDa protein isoform 1 of CUB domain-containing protein 1 (CDCP1) (FIG. 4B). CDCP1, also independently discovered as Trask (Bhatt et al 2005), is a heavily tyrosine phosphorylated protein that has been implicated in cancer invasiveness (Liu et al 2011, Uekita et al 2008, Wong et al 2009), suggesting that the effects of Dex.+Larg. treatment on this protein might be relevant to the anti-invasive properties of these drugs. Interestingly, all of the peptides identified were C-terminal to the known Matriptase cleavage site of CDCP1 (He et al 2010). CDCP1 cleavage is associated with its increased tyrosine phosphorylation, and the C-terminal, integral membrane fragment may mediate CDCP1 anti-adhesive activity (Brown et al 2004, He et al 2010). Matriptase cleavage of CDCP1 produces a C-terminal fragment of approximately 80 kDa, suggesting that Dex.+Larg. treatment may prevent proteolytic CDCP1 cleavage.

Example 5

Cleaved CDCP1 Associates with E-Cadherin

Immunoblot analysis with a CDCP1 antibody displayed the same pattern of bands observed with the anti-phosphotyrosine antibodies in which the full length form is present, but the cleaved form of CDCP1 (cCDCP1) is absent when the cells were treated with Dex.+Larg. (FIG. 5A). These results further support the notion that Dex.+Larg. treatment prevents CDCP1 cleavage. Immunoblot analysis of a panel of 14 human breast cancer cell lines showed that 11 of the lines exhibit a significant level of CDCP1 expression (FIG. 5B). The ratio between the full length and cleaved forms varies among the cell lines that express CDCP1. Immunoblot analysis of extracts from MDA-MB-231 or BT549 cells treated with various combinations of Dexamethasone, Largazole, and RU486 demonstrated that Dexamethasone blocks CDCP1 cleavage in the MDA-MB-231 cells and this is partially reversed by the Glucocorticoid Receptor antagonist RU486 (FIG. 5C). In contrast, in BT549 cells Dexamethasone decreased the total levels of CDCP1, and this effect is reversed by RU486. This suggests that Dexamethasone may have dual regulatory effects on CDCP1; in some cell lines blocking CDCP1 cleavage and in other lines blocking its expression.

Previous studies have shown that CDCP1 interacts with P-Cadherin and N-Cadherin (Bhatt et al 2005), however it is unknown whether CDCP1 interacts with E-Cadherin. E-Cadherin immunoprecipitation experiments showed that cCDCP1 interacts with E-Cadherin, and that Dex.+Larg. treatment blocks the formation of this complex by preventing CDCP1 cleavage (FIG. 5D). cCDCP1 was previously shown to bind to c-Src (Benes et al 2011, Bhatt et al 2005) and to participate in the tyrosine phosphorylation-dependent activation of PKCδ (Benes et al 2005). c-Src and PKCδ have both been implicated in the disruption of adherens junctions and in inducing cytoplasmic localization of E-Cadherin (Singh et al 2009). Therefore, it is tempting to speculate that cCDCP1 targets c-Src and PKCδ to adherens junctions, resulting in their dissolution, and that Dexamethasone prevents loss of cell-cell adhesion by blocking the proteolytic production of cCDCP1.

Example 6

HDAC Inhibitors Preferentially Increase E-Cadherin Association with γ-Catenin

Largazole did not influence CDCP1 cleavage, therefore we examined whether Largazole alters the subunit composition of E-Cadherin-containing complexes. These analyses indicated that Largazole preferentially increased γ-Catenin binding to E-Cadherin relative to β-Catenin binding (FIG. 6A) without changing the levels of γ-Catenin. In contrast, Dexamethasone did not increase γ-Catenin binding to E-Cadherin, but as expected, decreased cCDCP1 binding to E-Cadherin. Affinity purification of complexes containing E-Cadherin (E-Cad-GST) and γ-Catenin (γ-Cat-His$_6$) by sequential TALON and Glutathione-agarose chromatography further demonstrated that Dex.+Larg. treatment dramatically increased the stability of E-Cadherin/γ-Catenin complexes (FIG. 6B).

It is possible that Largazole alters E-Cadherin association with γ-Catenin through mechanisms that are independent of HDAC inhibition. Largazole requires a cysteine sulfhydryl group that inhibits HDAC activity by binding to its active site Zinc atom (Cole et al 2011, Liu et al 2010, Ying et al 2008a). In contrast, the HDAC inhibitors suberoylanilide hydroxamic acid (SAHA) and Trichostatin A (TSA) bind the active site Zinc atom via their hydroxamate moieties and are structurally very different from Largazole. Therefore it was reasoned that if Largazole increased E-Cadherin association with γ-Catenin by inhibiting HDAC activity then TSA and SAHA should have similar effects. Consistent with this idea, Largazole, SAHA, and TSA each stabilized E-Cadherin/γ-Catenin complexes to similar extents relative to vehicle treatment (FIG. 6C).

E-Cadherin as a Therapeutic Target in Invasive Cancers—

Previous studies have shown that overexpression of E-Cadherin in invasive breast cancer cell lines dramatically reduces their invasiveness in vitro (Wong and Gumbiner 2003), and this is consistent with our observations (FIG. 3B). However it is important to note that these same cells form tumors that invade extensively into the surrounding mammary tissue when grown as orthotopic xenografts (FIG. 1C). Further, E-Cadherin is expressed in a subset of invasive cancers (Boulos and Fedda 2011, Rakha et al 2010), and in some cases E-Cadherin expression correlates with a worse prognosis than intermediate levels of expression (Querzoli et al 2010). These observations indicate that the tumor- and invasion-suppressive functions of E-Cadherin are lost in many breast cancers independent of decreased expression. This suggests that it may be possible to identify drug combinations that restore E-Cadherin anticancer actions in this class of tumors.

Decreased E-Cadherin expression in human breast cancers is most commonly a result of epigenetic silencing rather than point mutations or chromosomal deletions. Therefore efforts have been directed toward using HDAC inhibitors to restore E-Cadherin expression in breast cancers (Ou et al 2007). However in both mouse and human basal-like breast cancer cell lines, E-Cadherin is frequently localized to perinuclear puncta rather than to the plasma membrane, and similar cytoplasmic localization is observed in clinical triple-negative breast cancer samples (Corsino et al 2008, Zhang et al 2009). This suggests that E-Cadherin expressed in basal-like breast cancer cells might not be functional even if it is expressed at high levels. The results in FIG. 1-6 employing MDA-MB-231 as a model cell line support this contention and indicate that a therapeutic approach for restoring E-Cadherin anticancer activity will require components that reverse epigenetic silencing of the E-Cadherin gene, Cdh1, and components that restore E-Cadherin function at the posttranslational level.

CDCP1 as a Novel Target of Dexamethasone Action—

Dexamethasone suppresses invasion through a number of different mechanisms (Buse et al 1995, Rubenstein et al 2003, Zettl et al 1992), however the present study is the first to our knowledge that links glucocorticoids to E-Cadherin through effects on CDCP1 cleavage. The mechanism by which Dexamethasone blocks CDCP1 cleavage is currently under investigation in our laboratory, but could involve decreased expression of the serine protease responsible for its cleavage, increased expression of a serine protease inhibitor, or decreased access of CDCP1 to the relevant protease. Future studies will also be required to determine to what extent regulation of CDCP1 cleavage or expression mediates the antiinvasive actions of glucocorticoids. It is also possible that blockade of CDCP1 cleavage suppresses invasion independently of E-Cadherin given that CDCP1 also binds to N- and P-Cadherin (Bhatt et al 2005), and that Dex.+Larg. blocks invasion in MDA-MB-231 cells which express very low levels of endogenous E-Cadherin (compare FIGS. 1D and 3B).

Increased E-Cadherin/γ-Catenin Complex Formation as a New Mechanism of HDAC Inhibitor Anticancer Activity—

HDAC inhibitors increase E-Cadherin expression in breast cancer cells where it has been epigenetically silenced (Ou et al 2007). Therefore, HDAC inhibitors may suppress cancer invasion both by increasing E-Cadherin expression, and by strengthening E-Cadherin association with γ-Catenin. To our knowledge, this is the first report that HDAC inhibitors facilitate the formation of E-Cadherin/γ-Catenin complexes. An interesting aspect of this observation is that Largazole had little effect on E-Cadherin association with β-Catenin even though γ- and β-Catenin are 69% identical and are thought to carry out redundant functions regarding the coupling of E-Cadherin to α-Catenin. γ-Catenin is the only protein known to be present in both adherens and desmosomal junctions. The formation of adherens junctions precedes the formation of desmosomal junctions during cell adhesion, and E-Cadherin/γ-Catenin association may facilitate the formation of desmosomal junctions (Lewis et al 1997). Therefore, it will be important to determine what influence, if any, HDAC inhibitors have on desmosomal junctions and the distribution of γ-Catenin between adherens versus desmosomal junctions.

The mechanism by which HDAC inhibitors aid the formation of E-Cadherin/γ-Catenin complexes is unclear and could involve increased acetylation of complex components. Along these lines, β-Catenin is regulated by acetylation (Levy et al 2004, Wolf et al 2002). Alternately, an indirect mechanism involving transcriptional regulation of components of the complex could be operative.

Potential Clinical Applications of Glucocorticoid and HDAC Inhibitor Combination Therapies—

Dexamethasone is currently administered before surgery to palliate the pain and nausea associated with mastectomies (Gomez-Hernandez et al 2010). The HDAC inhibitors Romidepsin (FK228) and Vorinostat (SAHA) are approved for the treatment of cutaneous T cell lymphoma. These and numerous other HDAC inhibitors are currently undergoing clinical study for efficacy against multiple types of human cancer. If glucocorticoids and HDAC inhibitors cooperate to suppress cancer invasion in animal models with acceptable side effects, then clinical trials in cancer patients may be warranted.

Triple-negative breast cancers as a category are largely overlapping with the basal-like subtype and are characterized by local invasion and high rates of postsurgical recurrence (Dawson et al 2009, Voduc et al 2010). These cancers frequently do not exhibit defined borders. Therefore recurrence is likely a result of incomplete surgical removal. It is possible that glucocorticoid and HDAC inhibitor combination therapy could be administered in the neoadjuvant setting to limit local invasion into the surrounding normal tissue and that this would reduce cancer relapse and improve patient survival rates.

The studies described here examine differences in E-Cadherin localization between luminal and basal-like breast cancer cell lines in order to discover mechanisms responsible for E-Cadherin mislocalization in invasive cancers. The results indicate that E-Cadherin forms complexes with the same proteins in both types of cell lines, but that the ratio between binding to γ-Catenin versus β-Catenin differs. MDA-MB-231 cells stably expressing E-Cadherin-Green Fluorescent Protein (E-Cad-GFP) or E-Cadherin-Glutathione S-Transferase (E-Cad-GST) fusion proteins were used as model systems to identify agents that cause relocalization of E-Cadherin from cytoplasmic vesicles to the plasma membrane, facilitate cell-cell adhesion, and block invasion. The glucocorticoid Dexamethasone and the novel Histone Deacetylase (HDAC) inhibitor Largazole (Taori et al 2008, Ying et al 2008b) were each found to partially restore E-Cadherin membrane localization and to suppress invasion, and the combination of these agents was more effective than either one alone. Dexamethasone was observed to block the cleavage of the pro-invasive protein CDCP1. This in turn prevented the preferential interaction of the cleaved form of CDCP1 with E-Cadherin. In contrast, HDAC inhibitors selectively increased E-Cadherin interaction with γ-Catenin versus β-Catenin. Together, the results show synergy between well-studied classes of drugs currently in clinical use that cooperate to restore E-Cadherin membrane localization and suppress the invasiveness of cancer cells, including triple-negative breast cancer cells.

REFERENCES

Baum B, Georgiou M (2011). Dynamics of adherens junctions in epithelial establishment, maintenance, and remodeling. *J Cell Biol* 192: 907-917.

Behrens J, Vakaet L, Friis R, Winterhager E, Van Roy F, Mareel M M et al (1993). Loss of epithelial differentiation and gain of invasiveness correlates with tyrosine phosphorylation of the E-cadherin/beta-catenin complex in cells transformed with a temperature-sensitive v-SRC gene. *J Cell Biol* 120: 757-766.

Benes C H, Wu N, Elia A E, Dharia T, Cantley L C, Soltoff S P (2005). The C2 domain of PKCdelta is a phosphotyrosine binding domain. *Cell* 121: 271-280.

Benes C H, Poulogiannis G, Cantley L C, Soltoff S P (2011). The SRC-associated protein CUB Domain-Containing Protein-1 regulates adhesion and motility. *Oncogene*.

Bhatt A S, Erdjument-Bromage H, Tempst P, Craik C S, Moasser M M (2005). Adhesion signaling by a novel mitotic substrate of src kinases. *Oncogene* 24: 5333-5343.

Boulos F, Fedda F (2011). Clinical and biological significance of E-cadherin protein expression in invasive lobular carcinoma of the breast. *Am J Surg Pathol* 35: 154-155.

Brown T A, Yang T M, Zaitsevskaia T, Xia Y, Dunn C A, Sigle R O et al (2004). Adhesion or plasmin regulates tyrosine phosphorylation of a novel membrane glycoprotein p80/gp140/CUB domain-containing protein 1 in epithelia. *J Biol Chem* 279: 14772-14783.

Buse P, Woo P L, Alexander D B, Reza A, Firestone G L (1995). Glucocorticoid-induced functional polarity of growth factor responsiveness regulates tight junction dynamics in transformed mammary epithelial tumor cells. *J Biol Chem* 270: 28223-28227.

Chytil A, Waltner-Law M, West R, Friedman D, Aakre M, Barker D et al (2004). Construction of a cyclin D1-Cdk2 fusion protein to model the biological functions of cyclin D1-Cdk2 complexes. *J Biol Chem* 279: 47688-47698.

Cole K E, Dowling D P, Boone M A, Phillips A J, Christianson D W (2011). Structural Basis of the Antiproliferative Activity of Largazole, a Depsipeptide Inhibitor of the Histone Deacetylases. *J Am Chem. Soc.*

Corsino P E, Davis B J, Norgaard P H, Parker N N, Law M, Dunn W et al (2008). Mammary tumors initiated by constitutive Cdk2 activation contain an invasive basal-like component. *Neoplasia* 10: 1240-1252.

Cowin P, Rowlands T M, Hatsell S J (2005). Cadherins and catenins in breast cancer. *Curr Opin Cell Biol* 17: 499-508.

Daniel J M (2007). Dancing in and out of the nucleus: p120(ctn) and the transcription factor Kaiso. *Biochim Biophys Acta* 1773: 59-68.

Dawson S J, Provenzano E, Caldas C (2009). Triple negative breast cancers: clinical and prognostic implications. *Eur J Cancer* 45 Suppl 1: 27-40.

Facina G, Lopes-Costa P V, Dos Santos A R, De Vasconcelos-Valenca R J, Pinho-Sobral A L, Ferreira-Filho C P et al (2010). Immunohistochemical expression of E-cadherin in sclerosing adenosis, ductal carcinoma in situ and invasive ductal carcinoma of the breast. *Diagn Cytopathol* 38: 235-238.

Gomez-Hernandez J, Orozco-Alatorre A L, Dominguez-Contreras M, Oceguera-Villanueva A, Gomez-Romo S, Alvarez Villasenor A S et al (2010). Preoperative dexamethasone reduces postoperative pain, nausea and vomiting following mastectomy for breast cancer. *BMC Cancer* 10: 692.

He T C, Zhou S, da Costa L T, Yu J, Kinzler K W, Vogelstein B (1998). A simplified system for generating recombinant adenoviruses. *Proc Natl Acad Sci USA* 95: 2509-2514.

He Y, Wortmann A, Burke L J, Reid J C, Adams M N, Abdul-Jabbar I et al (2010). Proteolysis-induced N-terminal ectodomain shedding of the integral membrane glycoprotein CUB domain-containing protein 1 (CDCP1) is accompanied by tyrosine phosphorylation of its C-terminal domain and recruitment of Src and PKCdelta. *J Biol Chem* 285: 26162-26173.

Heuberger J, Birchmeier W (2010). Interplay of cadherin-mediated cell adhesion and canonical Wnt signaling. *Cold Spring Harb Perspect Biol* 2: a002915.

Hiscox S, Jiang W G (1999). Association of the HGF/SF receptor, c-met, with the cell-surface adhesion molecule, E-cadherin, and catenins in human tumor cells. *Biochem Biophys Res Commun* 261: 406-411.

Ireton R C, Davis M A, van Hengel J, Mariner D J, Barnes K, Thoreson M A et al (2002). A novel role for p120 catenin in E-cadherin function. *J Cell Biol* 159: 465-476.

Jeanes A, Gottardi C J, Yap A S (2008). Cadherins and cancer: how does cadherin dysfunction promote tumor progression? *Oncogene* 27: 6920-6929.

Keller A, Nesvizhskii A I, Kolker E, Aebersold R (2002). Empirical statistical model to estimate the accuracy of peptide identifications made by MS/MS and database search. *Anal Chem* 74: 5383-5392.

Kinsella T M, Nolan G P (1996). Episomal vectors rapidly and stably produce high-titer recombinant retrovirus. *Hum Gene Ther* 7: 1405-1413.

Law B K, Chytil A, Dumont N, Hamilton E G, Waltner-Law M E, Aakre M E et al (2002). Rapamycin potentiates transforming growth factor beta-induced growth arrest in nontransformed, oncogene-transformed, and human cancer cells. *Mol Cell Biol* 22: 8184-8198.

Law M, Forrester E, Chytil A, Corsino P, Green G, Davis B et al (2006). Rapamycin disrupts cyclin/cyclin-dependent kinase/p21/proliferating cell nuclear antigen complexes and cyclin D1 reverses rapamycin action by stabilizing these complexes. *Cancer Res* 66: 1070-1080.

Levy L, Wei Y, Labalette C, Wu Y, Renard C A, Buendia M A et al (2004). Acetylation of beta-catenin by p300 regulates beta-catenin-Tcf4 interaction. *Mol Cell Biol* 24: 3404-3414.

Lewis J E, Wahl J K, 3rd, Sass K M, Jensen P J, Johnson K R, Wheelock M J (1997). Cross-talk between adherens junctions and desmosomes depends on plakoglobin. *J Cell Biol* 136: 919-934.

Liu H, Ong S E, Badu-Nkansah K, Schindler J, White F M, Hynes R O (2011). CUB-domain-containing protein 1 (CDCP1) activates Src to promote melanoma metastasis. *Proc Natl Acad Sci USA* 108: 1379-1384.

Liu Y, Salvador L A, Byeon S, Ying Y, Kwan J C, Law B K et al (2010). Anticolon cancer activity of largazole, a marine-derived tunable histone deacetylase inhibitor. *J Pharmacol Exp Ther* 335: 351-361.

Lombaerts M, van Wezel T, Philippo K, Dierssen J W, Zimmerman R M, Oosting J et al (2006). E-cadherin transcriptional downregulation by promoter methylation but not mutation is related to epithelial-to-mesenchymal transition in breast cancer cell lines. *Br J Cancer* 94: 661-671.

Matsuyoshi N, Hamaguchi M, Taniguchi S, Nagafuchi A, Tsukita S, Takeichi M (1992). Cadherin-mediated cell-cell adhesion is perturbed by v-src tyrosine phosphorylation in metastatic fibroblasts. *J Cell Biol* 118: 703-714.

Meyers M O, Klauber-Demore N, Ollila D W, Amos K D, Moore D T, Drobish A A et al (2011). Impact of Breast Cancer Molecular Subtypes on Locoregional Recurrence in Patients Treated with Neoadjuvant Chemotherapy for Locally Advanced Breast Cancer. *Ann Surg Oncol.*

Morgenstern J P, Land H (1990). Advanced mammalian gene transfer: high titre retroviral vectors with multiple drug selection markers and a complementary helper-free packaging cell line. *Nucleic Acids Res* 18: 3587-3596.

Nesvizhskii A I, Keller A, Kolker E, Aebersold R (2003). A statistical model for identifying proteins by tandem mass spectrometry. *Anal Chem* 75: 4646-4658.

Ou J N, Torrisani J, Unterberger A, Provencal N, Shikimi K, Karimi M et al (2007). Histone deacetylase inhibitor Trichostatin A induces global and gene-specific DNA demethylation in human cancer cell lines. *Biochem Pharmacol* 73: 1297-1307.

Papageorgis P, Lambert A W, Ozturk S, Gao F, Pan H, Manne U et al (2010). Smad signaling is required to maintain epigenetic silencing during breast cancer progression. *Cancer Res* 70: 968-978.

Pazaiti A, Fentiman I S (2011). Basal phenotype breast cancer: implications for treatment and prognosis. *Womens Health (Lond Engl)* 7: 181-202.

Querzoli P, Coradini D, Pedriali M, Boracchi P, Ambrogi F, Raimondi E et al (2010). An immunohistochemically positive E-cadherin status is not always predictive for a good prognosis in human breast cancer. *Br J Cancer* 103: 1835-1839.

Rakha E A, Patel A, Powe D G, Benhasouna A, Green A R, Lambros M B et al (2010). Clinical and biological significance of E-cadherin protein expression in invasive lobular carcinoma of the breast. *Am J Surg Pathol* 34: 1472-1479.

Rubenstein N M, Guan Y, Woo P L, Firestone G L (2003). Glucocorticoid downregulation of RhoA is required for the steroid-induced organization of the junctional complex and tight junction formation in rat mammary epithelial tumor cells. *J Biol Chem* 278: 10353-10360.

Sheffield J, Taylor N, Fauquet C, Chen S (2006). The cassava (*Manihot esculenta* Crantz) root proteome: protein identification and differential expression. *Proteomics* 6: 1588-1598.

Singh R, Lei P, Andreadis S T (2009). PKC-delta binds to E-cadherin and mediates EGF-induced cell scattering. *Exp Cell Res* 315: 2899-2913.

Swift S, Lorens J, Achacoso P, Nolan G P (2001). Rapid production of retroviruses for efficient gene delivery to mammalian cells using 293T cell-based systems. *Curr Protoc Immunol* Chapter 10: Unit 10 17C.

Taori K, Paul V J, Luesch H (2008). Structure and activity of largazole, a potent antiproliferative agent from the Floridian marine cyanobacterium *Symploca* sp. *J Am Chem Soc* 130: 1806-1807.

Uekita T, Tanaka M, Takigahira M, Miyazawa Y, Nakanishi Y, Kanai Y et al (2008). CUB-domain-containing protein 1 regulates peritoneal dissemination of gastric scirrhous carcinoma. *Am J Pathol* 172: 1729-1739.

Voduc K D, Cheang M C, Tyldesley S, Gelmon K, Nielsen T O, Kennecke H (2010). Breast cancer subtypes and the risk of local and regional relapse. *J Clin Oncol* 28: 1684-1691.

Wolf D, Rodova M, Miska E A, Calvet J P, Kouzarides T (2002). Acetylation of beta-catenin by CREB-binding protein (CBP). *J Biol Chem* 277: 25562-25567.

Wong A S, Gumbiner B M (2003). Adhesion-independent mechanism for suppression of tumor cell invasion by E-cadherin. *J Cell Biol* 161: 1191-1203.

Wong C H, Baehner F L, Spassov D S, Ahuja D, Wang D, Hann B et al (2009). Phosphorylation of the SRC epithelial substrate Trask is tightly regulated in normal epithelia but widespread in many human epithelial cancers. *Clin Cancer Res* 15: 2311-2322.

Ying Y, Liu Y, Byeon S R, Kim H, Luesch H, Hong J (2008a). Synthesis and activity of largazole analogues with linker and macrocycle modification. *Org Lett* 10: 4021-4024.

Ying Y, Taori K, Kim H, Hong J, Luesch H (2008b). Total synthesis and molecular target of largazole, a histone deacetylase inhibitor. *J Am Chem Soc* 130: 8455-8459.

Zettl K S, Sjaastad M D, Riskin P M, Parry G, Machen T E, Firestone G L (1992). Glucocorticoid-induced formation of tight junctions in mouse mammary epithelial cells in vitro. *Proc Natl Acad Sci USA* 89: 9069-9073.

Zhang X, Hashemi S S, Yousefi M, Gao C, Sheng J, Ni J et al (2009). Atypical E-cadherin expression in cell clusters overlying focally disrupted mammary myoepithelial cell layers: implications for tumor cell motility and invasion. *Pathol Res Pract* 205: 375-385.

Zhu M, Simons B, Zhu N, Oppenheimer D G, Chen S (2010). Analysis of abscisic acid responsive proteins in *Brassica napus* guard cells by multiplexed isobaric tagging. *J Proteomics* 73: 790-805.

FIGURE LEGENDS

Figure 2:
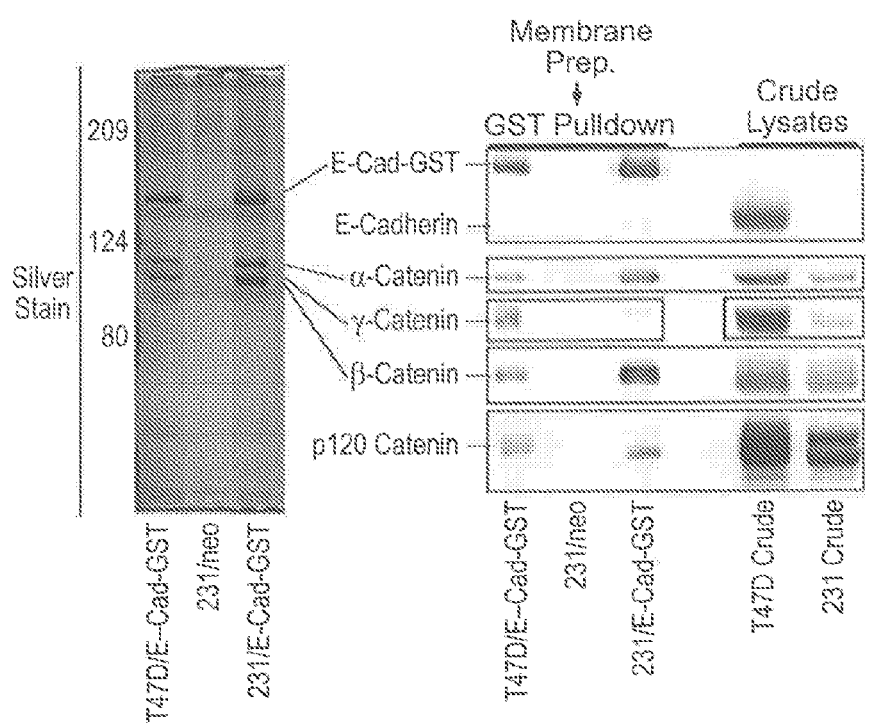
FIG. 2. depicts differences in E-Cadherin complexes isolated from noninvasive luminal and invasive basal-like human breast cancer cell lines FIG. 3. depicts results showing Dexamethasone (Dex) and Largazole (Larg) cooperate synergistically to suppress invasion and to restore E-Cadherin localization to the cell periphery FIG. 4. depicts results showing Dex.+Larg. blocks the production of the cleaved form of the pro-invasive protein CDCP1
Figure 2:
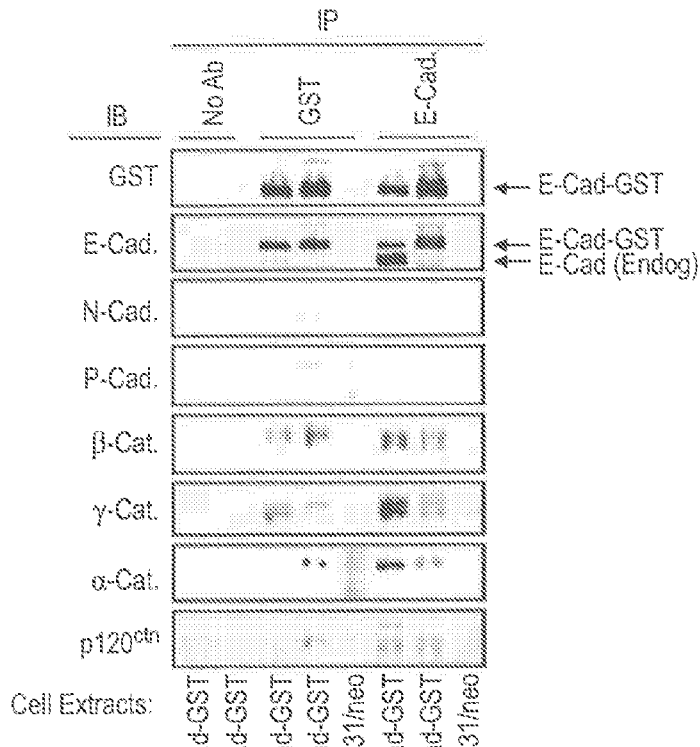
Figure 2:
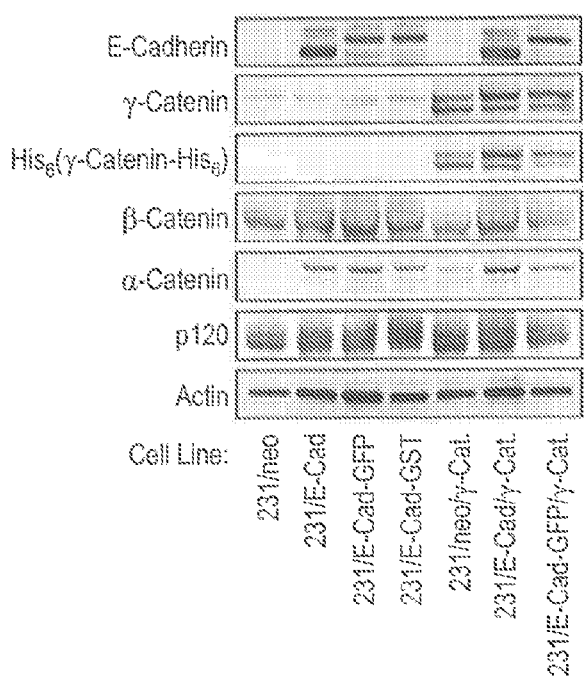

FIG. 1. Cellular models for studying E-Cadherin regulation in breast cancer cells in vitro and in vivo. A. Immunoblot analyses of MDA-MB-231 cells engineered to stably express E-Cadherin fused C-terminally to Green Fluorescent Protein (231/E-Cad-GFP), E-Cadherin fused C-terminally to Glutathione S-Transferase (231/E-Cad-GST), or stably transduced with the retroviral vector lacking an insert, but conferring Neomycin resistance (231/neo). The upper arrow represents the E-Cadherin-GST or -GFP fusion proteins and the lower arrow denotes endogenous E-Cadherin. B. Fluorescence microscopy of the indicated cell lines showing intracellular localization of the E-Cad-GFP fusion protein (green). C. Hematoxylin and Eosin stained sections of orthotopic xenograft tumors derived from the indicated cell lines displaying tumor invasion into the mouse mammary fat pad. Yellow arrows in the 231/E-Cad-GFP sample highlight the same region shown at low and high magnifications. D. Immunoblot analysis of a 231/E-Cad-GFP tumor extract demonstrating expression of the E-Cad-GFP fusion protein. The other samples are extracts of cultured cell lines serving as immunoblot controls. The Actin blot serves as a loading control.

FIG. 2. Differences in E-Cadherin complexes isolated from noninvasive luminal and invasive basal-like human breast cancer cell lines. A. E-Cadherin complexes were isolated from plasma membrane fractions by glutathione-agarose chromatography, resolved by SDS-PAGE, and visualized by silver stain (left panel). Proteomics studies were performed to identify E-Cadherin complex components (not shown) and immunoblot analysis was carried out with the indicated antibodies to verify the proteomics results (right panel). B. Immunoprecipitation was performed on the indicated cell extracts with antibodies to GST or E-Cadherin as indicated, and the immunoprecipitates were analyzed by immunoblot. C. Immunoblot analysis of the indicated stable cell lines.

Figure 3:
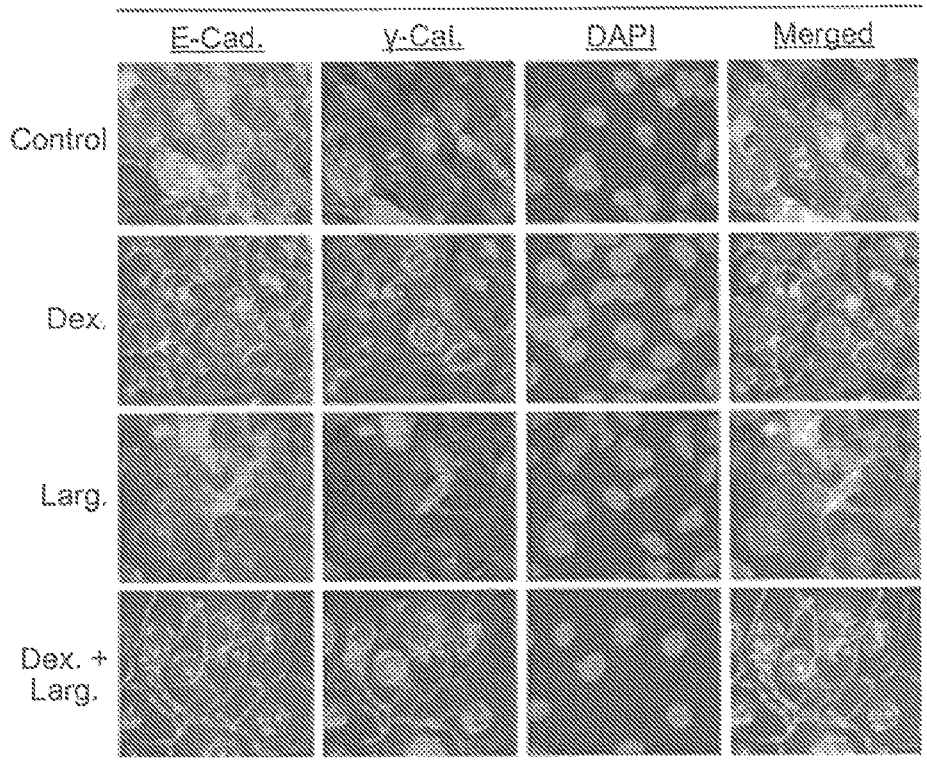
Figure 3:
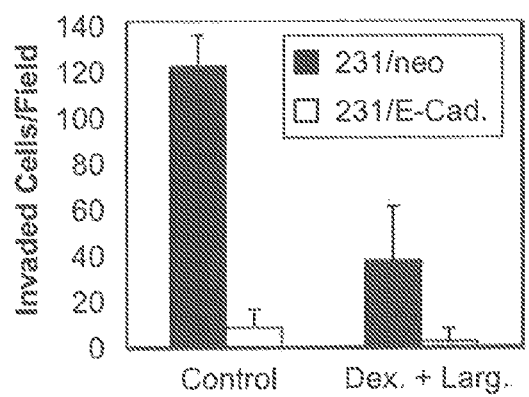
Figure 3:
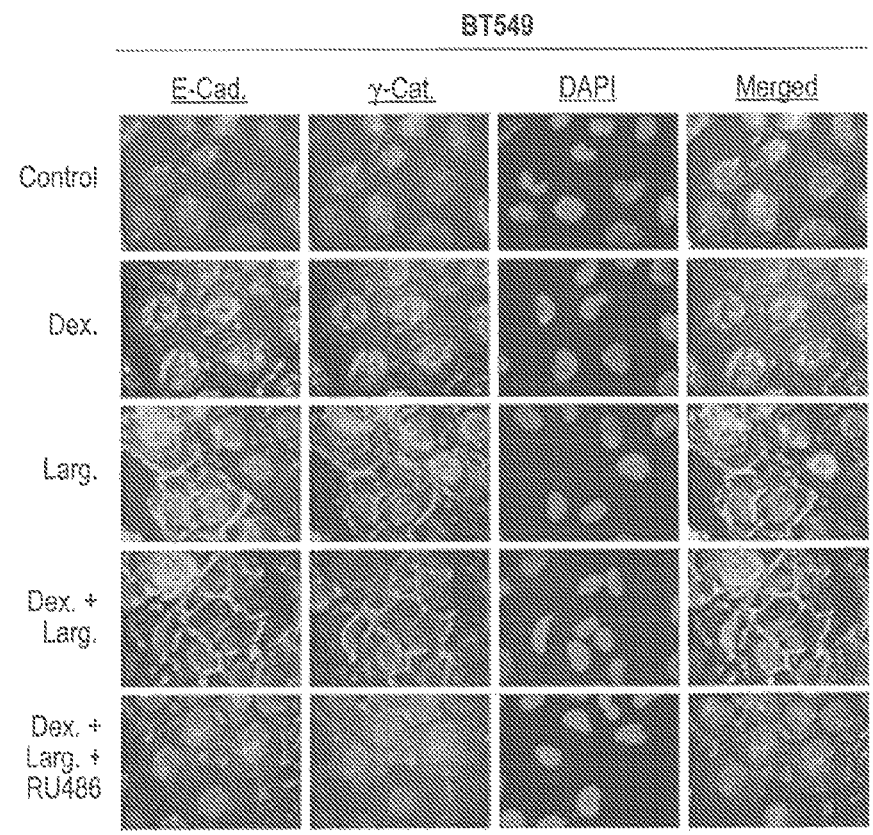
Figure 3:
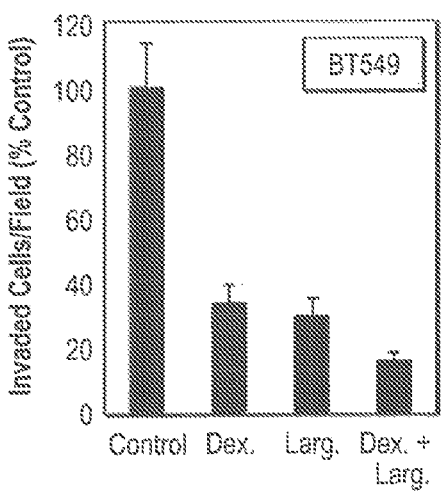

FIG. 3. Dexamethasone and Largazole cooperate to suppress invasion and to restore E-Cadherin localization to the cell periphery. A. Fluorescence (E-Cad-GFP) or immunofluorescence microscopy (γ-Catenin (γ-Cat.)) of 231/E-Cad-GFP cells treated for 72 hrs with Vehicle (Control), 100 nM Dexamethasone, 10 nM Largazole, or 100 nM Dexamethasone+10 nM Largazole (Dex.+Larg.). B. Invasion assays were performed on the indicated cell lines treated for 72 hrs with or without 100 nM Dexamethasone+10 nM Largazole using modified Boyden chambers impregnated with Matrigel. The results are presented as the average number of cells that invaded through the membrane per field±standard deviation of five randomly chosen fields, and are representative of three independently performed experiments. C. BT549 cells were treated and analyzed by immunofluorescence microscopy as in FIG. 3A. D. BT549 cells were treated as described in FIG. 3A and analyzed for invasion as outlined in FIG. 3B.

Figure 4:
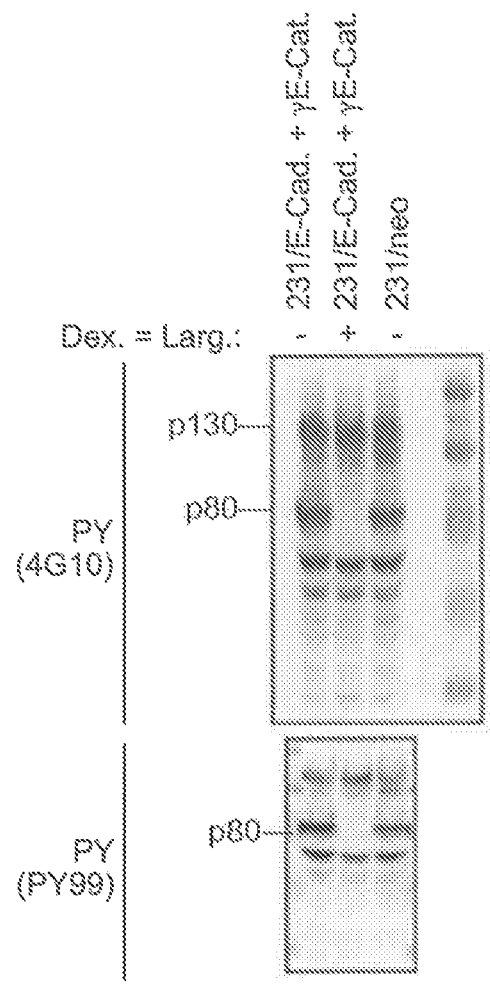

FIG. 4. Dex.+Larg. blocks the production of the cleaved form of the pro-invasive protein CDCP1. A. The indicated cell lines were treated for 72 hrs with or without Dex.+Larg. and extracts were analyzed by immunoblot with two different antiphosphotyrosine antibodies. B. An 80 kDa doublet corresponding to the band that disappears in antiphosphotyrosine immunoblots upon Dex.+Larg. treatment was immunopreciptated with an antiphosphotyrosine antibody (4G10) and identified by proteomics analyses. The tryptic peptides derived from the CDCP1 protein are underlined. The arrow shows the known Matriptase cleavage site present in CDCP1.

Figure 5:
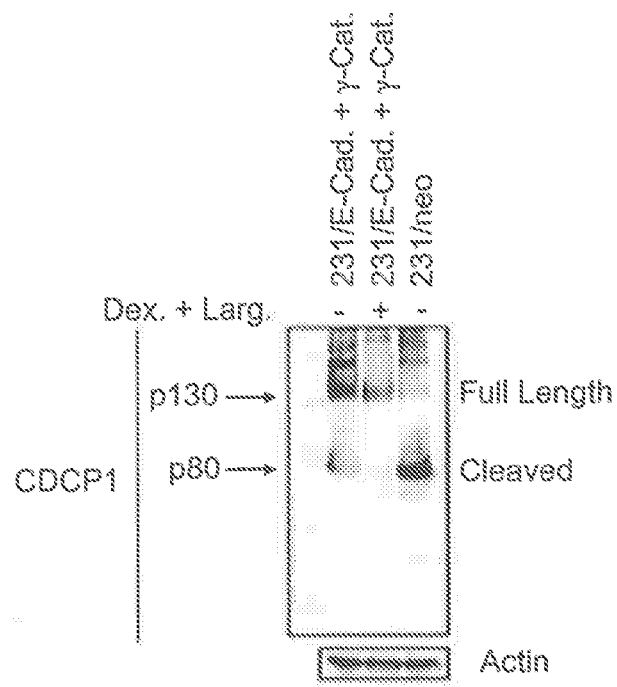
FIG. 5. depicts results showing E-Cadherin selectively interacts with the cleaved form of CDCP1
Figure 5:
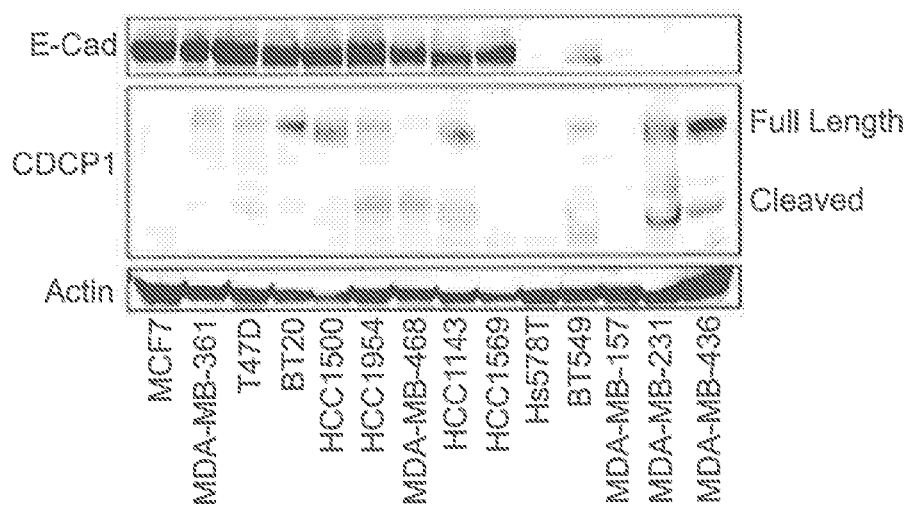
Figure 5:
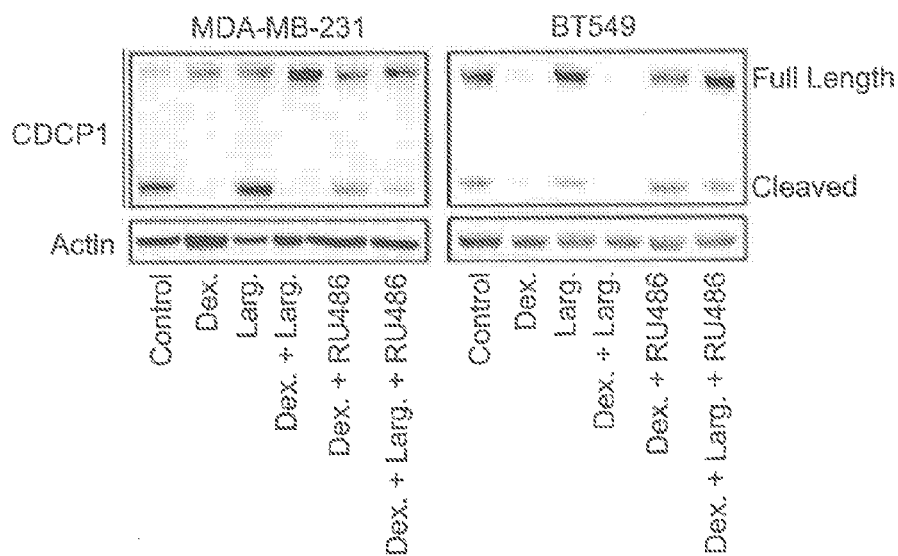
Figure 5:
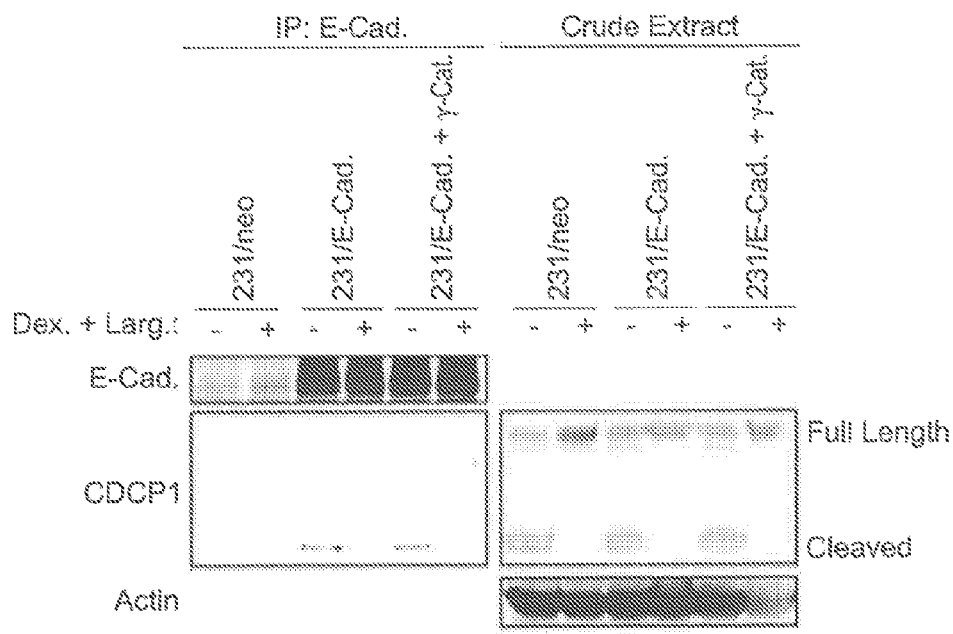

FIG. 5. E-Cadherin selectively interacts with the cleaved form of CDCP1. A. Immunoblot analysis of samples generated as in FIG. 4A with a CDCP1 antibody. p130 and p80 refer to the full length and cleaved forms of CDCP1. B. Immunoblot analysis of a panel of human breast cancer cell lines showing E-Cadherin expression and levels of the full length and cleaved forms of CDCP1. C. Immunoblot analysis showing the effects of the indicated 72 hr treatments with various combinations of Dexamethasone (100 nM), Largazole (10 nM), and RU486 (1 μM) on total levels of CDCP1 and CDCP1 cleavage in MDA-MB-231 and BT549 cells. D. Immunoblot analysis of E-Cadherin immunoprecipitates of the indicated cell lines treated with or without Dex.+Larg. for 72 hrs (left panel), and immunoblots of crude lysates corresponding to the same samples (right panel).

FIG. 6. HDAC inhibitors preferentially increase E-Cadherin interaction with γ-Catenin. A. Crude lysates (left panel) or GST pulldowns (right panel) from 231/E-Cad-GST cells treated for 72 hrs with 100 nM Dexamethasone, 10 nM Largazole, or Dex.+Larg. were analyzed by immunoblot. B. 231/E-Cad-GST cells were infected with an adenovirus encoding His$_6$-tagged γ-Catenin and 231/neo cells were infected with an adenovirus encoding GFP and incubated 24 hours. The cells were then treated as indicated for 72 hrs with or without Dex.+Larg. γ-Catenin- and E-Cadherin containing complexes were isolated by sequential TALON and glutathione-agarose chromatography and analyzed by immunoblot. C. 231/E-Cad-GST cells were treated with 10 nM Largazole, 1 μM SAHA, or 100 nM TSA for 72 hrs and extracts were subjected to glutathione-agarose chromatography and the affinity purified material was analyzed by immunoblot.

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed:

1. A method for treating breast cancer in a subject, comprising administering to the subject: 1) dexamethasone; and 2) a compound according to Formula I:

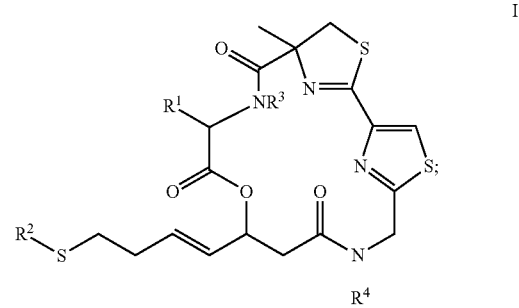

wherein:

each R is independently H or alkyl;

each $R^1$ is independently H or alkyl;

each $R^2$ is independently H, alkyl, or C(O)R;

each $R^3$ is independently H, alkyl, C(O)OR, or C(O)NRR;

each $R^4$ is independently H, alkyl, C(O)OR, or C(O)NRR;

and pharmaceutically acceptable salts thereof.

2. The method of claim 1, wherein $R^3$ and $R^4$ are H.

3. The method of claim 2 wherein $R^1$ is isopropyl.

4. The method of claim 1, wherein the compound of Formula I is any of Compounds B1-B8 in Table B:

TABLE B

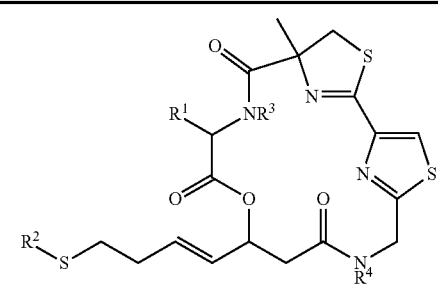

| Cmpd No. | $R^1$ | $R^2$ | $R^3$ | $R^4$ |
|---|---|---|---|---|
| B1 | isopropyl | n-heptylC(O)— | H | H |
| B2 | isopropyl | n-heptylC(O)— | H | Me |

TABLE B-continued

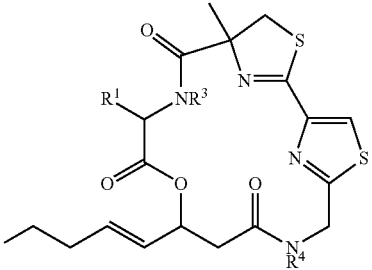

| Cmpd No. | R$^1$ | R$^2$ | R$^3$ | R$^4$ |
|---|---|---|---|---|
| B3 | isopropyl | Me | H | H |
| B4 | isopropyl | n-heptylC(O)— | H | methylC(O)— |
| B5 | isopentyl | n-heptylC(O)— | H | H |
| B6 | ethyl | n-heptylC(O)— | Me | Me |
| B7 | isopropyl | CH$_3$C(O)— | H | H |
| B8 | isopropyl | H | H | H. |

5. The method of claim 1 wherein the compound of Formula I is largazole.

6. The method of claim 1, wherein R$^2$ is alkyl.

7. The method of claim 6, wherein R$^2$ is alkylC(O)—.

8. A pharmaceutical composition comprising: 1) dexamethasone; and 2) a compound of Formula I, or salt thereof, and a pharmaceutically acceptable carrier;

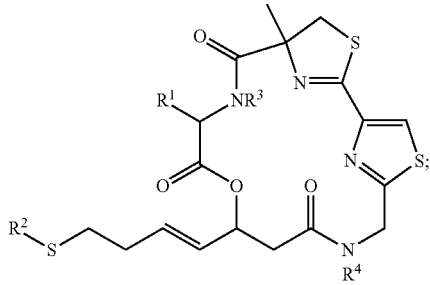

wherein:
each R is independently H or alkyl;
each R$^1$ is independently H or alkyl;
each R$^2$ is independently H, alkyl, or C(O)R;
each R$^3$ is independently H, alkyl, C(O)OR, or C(O)NRR;
each R$^4$ is independently H, alkyl, C(O)OR, or C(O)NRR.

9. A pharmaceutical composition comprising: 1) dexamethasone; and 2) any of Compounds A1-A8 in Table A:

TABLE A

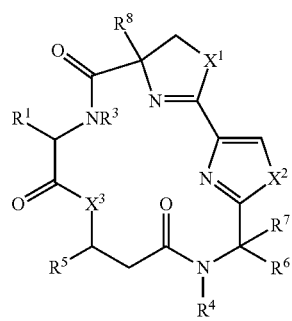

| No | R$^1$ | R$^2$ | R$^3$ | R$^4$ | R$^5$ | R$^6$ | R$^7$ | R$^8$ | R$^9$ | R$^{10}$ | n | X$^1$ | X$^2$ | X$^3$ |
|---|---|---|---|---|---|---|---|---|---|---|---|---|---|---|
| A1 | iPr | —SC(O)Me | H | H | (R$^{5"}$) | H | H | CH$_3$ | — | — | 4 | S | S | O |
| A2 | iPr | —SC(O)Me | H | H | (R$^{5'}$) | H | H | CH$_3$ | — | — | 3 | S | S | O |
| A3 | iPr | (HO)NHC(O)— | H | H | (R$^{5'}$) | H | H | CH$_3$ | — | — | 2 | S | S | O |
| A4 | iPr | MeC(O)N | H | H | (R$^{5'}$) | H | H | CH$_3$ | — | — | 2 | S | S | O |
| A5 | iPr | —SSR$^9$ | H | H | (R$^{5'}$) | H | H | CH$_3$ | — | — | 2 | S | S | O |
| A6 | iPr | —SSMe | H | H | (R$^{5"}$) | H | H | CH$_3$ | — | — | 4 | S | S | O |
| A7 | iPr | —SC(O)Me | H | H | (R$^{5"}$) | H | H | CH$_3$ | — | — | 4 | S | S | O |
| A8 | iPr | —SSR$^9$ | H | H | (R$^{5'}$) | H | H | CH$_3$ | (C) | — | 2 | S | S | O |

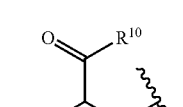

wherein (C) is

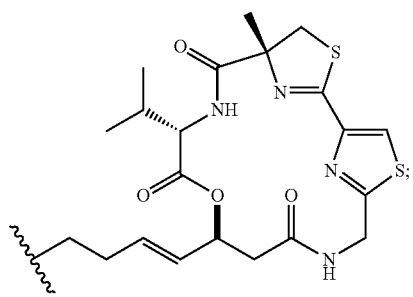

R⁵' is

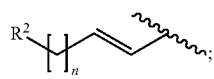

R⁵'' is

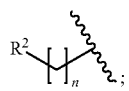

or any of Compounds B1-B8 in Table B,

TABLE B

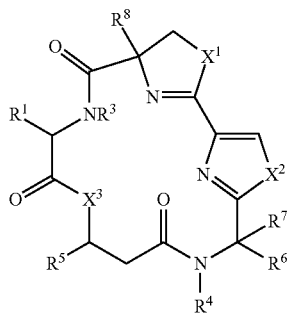

| Cmpd No. | R¹ | R² | R³ | R⁴ |
|---|---|---|---|---|
| B1 | isopropyl | n-heptylC(O)— | H | H |
| B2 | isopropyl | n-heptylC(O)— | H | Me |
| B3 | isopropyl | Me | H | H |
| B4 | isopropyl | n-heptylC(O)— | H | methylC(O)— |
| B5 | isopentyl | n-heptylC(O)— | H | H |

TABLE B-continued

| Cmpd No. | R¹ | R² | R³ | R⁴ |
|---|---|---|---|---|
| B6 | ethyl | n-heptylC(O)— | Me | Me |
| B7 | isopropyl | CH₃C(O)— | H | H |
| B8 | isopropyl | H | H | H | and a pharmaceutically acceptable carrier.

10. The pharmaceutical composition of claim 9 further comprising an additional anti-cancer agent.

11. A kit comprising an effective amount of: 1) dexamethasone; and 2) a compound of Formula I, or a salt thereof, in unit dosage form, together with instructions for administering the compound to a subject suffering from or susceptible to breast cancer;

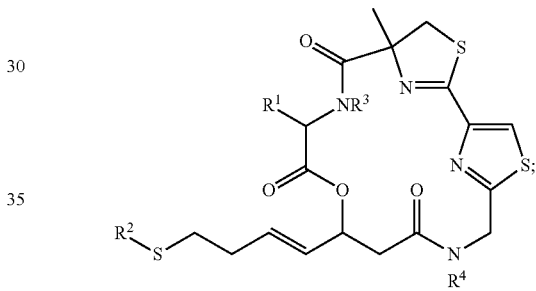

I wherein:
each R is independently H or alkyl;
each R¹ is independently H or alkyl;
each R² is independently H, alkyl, or C(O)R;
each R³ is independently H, alkyl, C(O)OR, or C(O)NRR;
each R⁴ is independently H, alkyl, C(O)OR, or C(O)NRR.

12. A method of treating breast cancer in a subject, comprising contacting the subject with: 1) dexamethasone; and 2) any of Compounds A1-A8 in Table A:

TABLE A

| No | R¹ | R² | R³ | R⁴ | R⁵ | R⁶ | R⁷ | R⁸ | R⁹ | R¹⁰ | n | X¹ | X² | X³ |
|---|---|---|---|---|---|---|---|---|---|---|---|---|---|---|
| A1 | iPr | —SC(O)Me | H | H | (R⁵'') | H | H | CH₃ | — | — | 4 | S | S | O |
| A2 | iPr | —SC(O)Me | H | H | (R⁵') | H | H | CH₃ | — | — | 3 | S | S | O |

TABLE A-continued

[Structure shown: macrocyclic compound with R¹, R³, R⁴, R⁵, R⁶, R⁷, R⁸, X¹, X², X³ substituents]

| No | R¹ | R² | R³ | R⁴ | R⁵ | R⁶ | R⁷ | R⁸ | R⁹ | R¹⁰ | n | X¹ | X² | X³ |
|---|---|---|---|---|---|---|---|---|---|---|---|---|---|---|
| A3 | iPr | (HO)NHC(O)— | H | H | (R⁵') | H | H | CH₃ | — | — | 2 | S | S | O |
| A4 | iPr | MeC(O)NH(OH)— | H | H | (R⁵') | H | H | CH₃ | — | — | 2 | S | S | O |
| A5 | iPr | —SSR⁹ | H | H | (R⁵') | H | H | CH₃ | [structure with R¹⁰, H₂N] | OH | 2 | S | S | O |
| A6 | iPr | —SSMe | H | H | (R⁵″) | H | H | CH₃ | — | — | 4 | S | S | O |
| A7 | iPr | —SC(O)Me | H | H | (R⁵″) | H | H | CH₃ | — | — | 4 | S | S | O |
| A8 | iPr | —SSR⁹ | H | H | (R⁵') | H | H | CH₃ | (C) | — | 2 | S | S | O | wherein (C) is (C) [structure shown]

R⁵' is

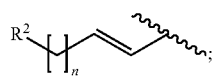

R⁵″ is

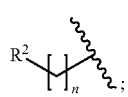

or any of Compounds B1–B8 in Table B,

TABLE B

[Structure shown with R¹, R², R³, R⁴ substituents]

| Cmpd No. | R¹ | R² | R³ | R⁴ |
|---|---|---|---|---|
| B1 | isopropyl | n-heptylC(O)— | H | H |
| B2 | isopropyl | n-heptylC(O)— | H | Me |
| B3 | isopropyl | Me | H | H |
| B4 | isopropyl | n-heptylC(O)— | H | methylC(O)— |
| B5 | isopentyl | n-heptylC(O)— | H | H |
| B6 | ethyl | n-heptylC(O)— | Me | Me |
| B7 | isopropyl | CH₃C(O)— | H | H |
| B8 | isopropyl | H | H | H | in an amount and under conditions sufficient to treat breast cancer in the subject.

13. The method of claim 12, wherein the compounds are dexamethasone and largazole.

14. The method of claim 12, wherein the subject is a mammal.

15. The method of claim 12, wherein the subject is a primate or human.

* * * * *